US008608043B2

(12) United States Patent
Scirica

(10) Patent No.: US 8,608,043 B2
(45) Date of Patent: Dec. 17, 2013

(54) SURGICAL INSTRUMENT HAVING A MULTI-LAYERED DRIVE BEAM

(75) Inventor: Paul Scirica, Huntington, CT (US)

(73) Assignee: Covidien LP, Mansfield, MA (US)

( * ) Notice: Subject to any disclaimer, the term of this patent is extended or adjusted under 35 U.S.C. 154(b) by 1703 days.

(21) Appl. No.: 11/544,518

(22) Filed: Oct. 6, 2006

(65) Prior Publication Data

US 2008/0083808 A1    Apr. 10, 2008

(51) Int. Cl.
*A61B 17/10*  (2006.01)

(52) U.S. Cl.
USPC ......................................... 227/175.1; 227/19

(58) Field of Classification Search
USPC .......................... 227/175.1, 179.1, 176.1, 19
See application file for complete search history.

(56) References Cited

U.S. PATENT DOCUMENTS

| | | |
|---|---|---|
| 3,079,606 A | 3/1963 | Bobrov et al. |
| 3,490,675 A | 1/1970 | Green et al. |
| 3,777,538 A | 12/1973 | Weatherly et al. |
| 4,027,510 A | 6/1977 | Hiltebrandt |
| 4,086,926 A | 5/1978 | Green et al. |
| 4,244,372 A | 1/1981 | Kapitanov et al. |
| 4,429,695 A | 2/1984 | Green |
| 4,505,414 A | 3/1985 | Filipi |
| 4,589,413 A | 5/1986 | Malyshev et al. |
| 4,602,634 A | 7/1986 | Barkley |
| 4,608,981 A | 9/1986 | Rothfuss et al. |
| 4,610,383 A | 9/1986 | Rothfuss et al. |
| 4,633,861 A | 1/1987 | Chow et al. |
| 4,633,874 A | 1/1987 | Chow et al. |
| 4,671,445 A | 6/1987 | Barker et al. |
| 4,700,703 A | 10/1987 | Resnick et al. |
| 4,703,887 A | 11/1987 | Clanton et al. |
| 4,728,020 A | 3/1988 | Green et al. |
| 4,752,024 A | 6/1988 | Green et al. |
| 4,784,137 A | 11/1988 | Kulik et al. |
| 4,863,088 A | 9/1989 | Redmond et al. |
| 4,892,244 A | 1/1990 | Fox et al. |

(Continued)

FOREIGN PATENT DOCUMENTS

| | | |
|---|---|---|
| AU | 5476586 | 9/1986 |
| DE | 2744824 | 4/1978 |

(Continued)

OTHER PUBLICATIONS

International Search Report for PCT/US2007/021493 date of completion is Mar. 4, 2008 (13 pages).

(Continued)

*Primary Examiner* — Brian D Nash

(57) ABSTRACT

A surgical instrument including a handle portion, a body portion, a movable handle, a tool assembly, a drive beam and a closure apparatus is disclosed. The movable handle is in mechanical cooperation with a drive member. The tool assembly includes an anvil, a cartridge assembly and a contact surface. The drive beam includes a plurality of layers and at least one layer has a proximal engagement portion and is configured to engage a portion of the drive member. The closure apparatus is configured to engage the contact surface of the tool assembly. At least a partial actuation of the movable handle moves the closure apparatus distally into engagement with the contact surface to approximate the anvil and the cartridge assembly. At least one of the layers of the drive beam is affixed to an adjacent layer of the drive beam via at least one spot weld.

21 Claims, 28 Drawing Sheets

(56) References Cited

U.S. PATENT DOCUMENTS

| | | |
|---|---|---|
| 4,978,049 A | 12/1990 | Green |
| 4,991,764 A | 2/1991 | Mericle |
| 5,040,715 A | 8/1991 | Green et al. |
| 5,065,929 A | 11/1991 | Schulze et al. |
| 5,074,454 A | 12/1991 | Peters |
| 5,083,695 A | 1/1992 | Foslien et al. |
| 5,084,057 A | 1/1992 | Green et al. |
| 5,111,987 A | 5/1992 | Moeinzadeh et al. |
| 5,129,570 A | 7/1992 | Schulze et al. |
| 5,141,144 A | 8/1992 | Foslien et al. |
| 5,170,925 A | 12/1992 | Madden et al. |
| 5,171,247 A | 12/1992 | Hughetti et al. |
| 5,246,156 A | 9/1993 | Rothfuss et al. |
| RE34,519 E | 1/1994 | Fox et al. |
| 5,282,807 A | 2/1994 | Knoepfler |
| 5,307,976 A | 5/1994 | Olson et al. |
| 5,312,023 A | 5/1994 | Green et al. |
| 5,318,221 A | 6/1994 | Green et al. |
| 5,326,013 A | 7/1994 | Green et al. |
| 5,328,077 A | 7/1994 | Lou |
| 5,332,142 A | 7/1994 | Robinson et al. |
| 5,336,232 A | 8/1994 | Green et al. |
| 5,358,506 A | 10/1994 | Green et al. |
| 5,364,001 A | 11/1994 | Bryan |
| 5,364,002 A | 11/1994 | Green et al. |
| 5,364,003 A | 11/1994 | Williamson, IV |
| 5,376,095 A | 12/1994 | Ortiz |
| 5,381,943 A | 1/1995 | Allen et al. |
| 5,382,255 A | 1/1995 | Castro et al. |
| 5,383,880 A | 1/1995 | Hooven |
| 5,389,098 A | 2/1995 | Tsuruta et al. |
| 5,395,033 A | 3/1995 | Byrne et al. |
| 5,395,034 A | 3/1995 | Allen et al. |
| 5,397,046 A | 3/1995 | Savage et al. |
| 5,397,324 A | 3/1995 | Carroll et al. |
| 5,407,293 A | 4/1995 | Crainich |
| 5,413,268 A | 5/1995 | Green et al. |
| 5,415,334 A | 5/1995 | Williamson, IV et al. |
| 5,415,335 A | 5/1995 | Knodell, Jr. |
| 5,417,361 A | 5/1995 | Williamson, IV |
| 5,423,471 A | 6/1995 | Mastri et al. |
| 5,425,745 A | 6/1995 | Green et al. |
| 5,431,322 A | 7/1995 | Green et al. |
| 5,431,323 A | 7/1995 | Smith et al. |
| 5,433,721 A | 7/1995 | Hooven et al. |
| 5,447,265 A | 9/1995 | Vidal et al. |
| 5,452,837 A | 9/1995 | Williamson, IV et al. |
| 5,456,401 A | 10/1995 | Green et al. |
| 5,464,300 A | 11/1995 | Crainich |
| 5,465,895 A | 11/1995 | Knodel et al. |
| 5,467,911 A | 11/1995 | Tsuruta et al. |
| 5,470,007 A | 11/1995 | Plyley et al. |
| 5,470,010 A | 11/1995 | Rothfuss et al. |
| 5,472,132 A | 12/1995 | Savage et al. |
| 5,474,566 A | 12/1995 | Alesi et al. |
| 5,476,206 A | 12/1995 | Green et al. |
| 5,478,003 A | 12/1995 | Green et al. |
| 5,480,089 A | 1/1996 | Blewett |
| 5,482,197 A | 1/1996 | Green et al. |
| 5,484,095 A | 1/1996 | Green et al. |
| 5,484,451 A | 1/1996 | Akopov et al. |
| 5,485,952 A | 1/1996 | Fontayne |
| 5,486,185 A | 1/1996 | Freitas et al. |
| 5,487,499 A | 1/1996 | Sorrentino et al. |
| 5,487,500 A | 1/1996 | Knodel et al. |
| 5,489,058 A | 2/1996 | Plyley et al. |
| 5,497,933 A | 3/1996 | DeFonzo et al. |
| 5,505,363 A | 4/1996 | Green et al. |
| 5,507,426 A | 4/1996 | Young et al. |
| 5,518,163 A | 5/1996 | Hooven |
| 5,518,164 A | 5/1996 | Hooven |
| 5,529,235 A | 6/1996 | Boiarski et al. |
| 5,531,744 A | 7/1996 | Nardella et al. |
| 5,535,934 A | 7/1996 | Boiarski et al. |
| 5,535,935 A | 7/1996 | Vidal et al. |
| 5,535,937 A | 7/1996 | Boiarski et al. |
| 5,540,375 A | 7/1996 | Bolanos et al. |
| 5,551,622 A | 9/1996 | Yoon |
| 5,553,765 A | 9/1996 | Knodel et al. |
| 5,554,164 A | 9/1996 | Wilson et al. |
| 5,554,169 A | 9/1996 | Green et al. |
| 5,560,530 A | 10/1996 | Bolanos et al. |
| 5,560,532 A | 10/1996 | DeFonzo et al. |
| 5,562,239 A | 10/1996 | Boiarski et al. |
| 5,562,241 A | 10/1996 | Knodel et al. |
| 5,562,682 A | 10/1996 | Oberlin et al. |
| 5,564,615 A | 10/1996 | Bishop et al. |
| 5,571,116 A | 11/1996 | Bolanos et al. |
| 5,573,543 A | 11/1996 | Akopov et al. |
| 5,575,799 A | 11/1996 | Bolanos et al. |
| 5,577,654 A | 11/1996 | Bishop |
| 5,579,107 A | 11/1996 | Wright et al. |
| 5,584,425 A | 12/1996 | Savage et al. |
| 5,586,711 A | 12/1996 | Plyley et al. |
| 5,588,580 A | 12/1996 | Paul et al. |
| 5,588,581 A | 12/1996 | Conlon et al. |
| 5,597,107 A | 1/1997 | Knodel et al. |
| 5,601,224 A | 2/1997 | Bishop et al. |
| 5,607,095 A | 3/1997 | Smith et al. |
| 5,615,820 A | 4/1997 | Viola |
| 5,618,291 A | 4/1997 | Thompson et al. |
| 5,624,452 A | 4/1997 | Yates |
| 5,626,587 A | 5/1997 | Bishop et al. |
| 5,628,446 A | 5/1997 | Geiste et al. |
| 5,630,539 A | 5/1997 | Plyley et al. |
| 5,630,540 A | 5/1997 | Blewett |
| 5,630,541 A | 5/1997 | Williamson, IV et al. |
| 5,632,432 A | 5/1997 | Schulze et al. |
| 5,634,584 A | 6/1997 | Okorocha et al. |
| 5,636,780 A | 6/1997 | Green et al. |
| 5,645,209 A | 7/1997 | Green et al. |
| 5,647,526 A | 7/1997 | Green et al. |
| 5,653,374 A | 8/1997 | Young et al. |
| 5,653,721 A | 8/1997 | Knodel et al. |
| 5,655,698 A | 8/1997 | Yoon |
| 5,657,921 A | 8/1997 | Young et al. |
| 5,658,300 A | 8/1997 | Bito et al. |
| 5,662,258 A | 9/1997 | Knodel et al. |
| 5,662,259 A | 9/1997 | Yoon |
| 5,662,260 A | 9/1997 | Yoon |
| 5,662,662 A | 9/1997 | Bishop et al. |
| 5,662,666 A | 9/1997 | Onuki et al. |
| 5,667,517 A | 9/1997 | Hooven |
| 5,669,544 A | 9/1997 | Schulze et al. |
| 5,673,840 A | 10/1997 | Schulze et al. |
| 5,673,841 A | 10/1997 | Schulze et al. |
| 5,673,842 A | 10/1997 | Bittner et al. |
| 5,676,674 A | 10/1997 | Bolanos et al. |
| 5,680,981 A | 10/1997 | Mililli et al. |
| 5,680,982 A | 10/1997 | Schulze et al. |
| 5,690,269 A | 11/1997 | Bolanos et al. |
| 5,692,668 A | 12/1997 | Schulze et al. |
| 5,697,542 A | 12/1997 | Knodel et al. |
| 5,704,534 A | 1/1998 | Huitema et al. |
| 5,706,997 A | 1/1998 | Green et al. |
| 5,709,334 A | 1/1998 | Sorrentino et al. |
| 5,711,472 A | 1/1998 | Bryan |
| 5,713,505 A | 2/1998 | Huitema |
| 5,716,366 A | 2/1998 | Yates |
| 5,725,536 A | 3/1998 | Oberlin et al. |
| 5,725,554 A | 3/1998 | Simon et al. |
| 5,728,110 A | 3/1998 | Vidal et al. |
| 5,735,848 A | 4/1998 | Yates et al. |
| 5,743,456 A | 4/1998 | Jones et al. |
| 5,749,893 A | 5/1998 | Vidal et al. |
| 5,752,644 A | 5/1998 | Bolanos et al. |
| 5,762,255 A | 6/1998 | Chrisman et al. |
| 5,762,256 A | 6/1998 | Mastri et al. |
| 5,769,303 A | 6/1998 | Knodel et al. |
| 5,772,673 A | 6/1998 | Cuny et al. |
| 5,779,130 A | 7/1998 | Alesi et al. |
| 5,779,131 A | 7/1998 | Knodel et al. |
| 5,779,132 A | 7/1998 | Knodel et al. |
| 5,782,396 A | 7/1998 | Mastri et al. |

(56) References Cited

U.S. PATENT DOCUMENTS

| | | |
|---|---|---|
| 5,782,397 A | 7/1998 | Koukline |
| 5,782,834 A | 7/1998 | Lucey et al. |
| 5,797,536 A | 8/1998 | Smith et al. |
| 5,797,537 A | 8/1998 | Oberlin et al. |
| 5,797,538 A | 8/1998 | Heaton et al. |
| 5,810,811 A | 9/1998 | Yates et al. |
| 5,810,855 A | 9/1998 | Rayburn et al. |
| 5,814,055 A | 9/1998 | Knodel et al. |
| 5,816,471 A | 10/1998 | Plyley et al. |
| 5,817,109 A | 10/1998 | McGarry et al. |
| 5,820,009 A | 10/1998 | Melling et al. |
| 5,823,066 A | 10/1998 | Huitema et al. |
| 5,826,776 A | 10/1998 | Schulze et al. |
| 5,829,662 A | 11/1998 | Allen et al. |
| 5,833,695 A | 11/1998 | Yoon |
| 5,836,147 A | 11/1998 | Schnipke |
| 5,862,972 A | 1/1999 | Green et al. |
| 5,865,361 A | 2/1999 | Milliman et al. |
| 5,871,135 A | 2/1999 | Williamson, IV et al. |
| 5,873,873 A | 2/1999 | Smith et al. |
| 5,897,562 A | 4/1999 | Bolanos et al. |
| 5,901,895 A | 5/1999 | Heaton et al. |
| 5,911,353 A | 6/1999 | Bolanos et al. |
| 5,918,791 A | 7/1999 | Sorrentino et al. |
| 5,919,198 A | 7/1999 | Graves, Jr. et al. |
| 5,922,001 A | 7/1999 | Yoon |
| 5,954,259 A | 9/1999 | Viola et al. |
| 5,980,510 A | 11/1999 | Tsonton et al. |
| 6,004,335 A | 12/1999 | Vaitekunas et al. |
| 6,010,054 A | 1/2000 | Johnson et al. |
| 6,032,849 A | 3/2000 | Mastri et al. |
| 6,079,606 A | 6/2000 | Milliman et al. |
| 6,109,500 A | 8/2000 | Alli et al. |
| 6,197,017 B1 | 3/2001 | Brock et al. |
| 6,202,914 B1 | 3/2001 | Geiste et al. |
| 6,241,139 B1 | 6/2001 | Milliman et al. |
| 6,250,532 B1 | 6/2001 | Green et al. |
| 6,264,086 B1 | 7/2001 | McGuckin, Jr. |
| 6,264,087 B1 | 7/2001 | Whitman |
| 6,269,977 B1 | 8/2001 | Moore |
| 6,279,809 B1 | 8/2001 | Nicolo |
| 6,315,183 B1 | 11/2001 | Piraka |
| 6,315,184 B1 | 11/2001 | Whitman |
| 6,325,810 B1 | 12/2001 | Hamilton et al. |
| 6,330,965 B1 | 12/2001 | Milliman et al. |
| 6,436,097 B1 | 8/2002 | Nardella |
| 6,439,446 B1 | 8/2002 | Perry et al. |
| 6,443,973 B1 | 9/2002 | Whitman |
| 6,463,623 B2 | 10/2002 | Ahn et al. |
| 6,488,196 B1 | 12/2002 | Fenton, Jr. |
| 6,503,257 B2 | 1/2003 | Grant et al. |
| 6,505,768 B2 | 1/2003 | Whitman |
| 6,544,274 B2 | 4/2003 | Danitz et al. |
| 6,554,844 B2 | 4/2003 | Lee et al. |
| 6,565,554 B1 | 5/2003 | Niemeyer |
| 6,587,750 B2 | 7/2003 | Gerbi et al. |
| 6,592,597 B2 | 7/2003 | Grant et al. |
| 6,594,552 B1 | 7/2003 | Nowlin et al. |
| 6,602,252 B2 | 8/2003 | Mollenauer |
| 6,612,053 B2 | 9/2003 | Liao |
| 6,619,529 B2 | 9/2003 | Green et al. |
| 6,644,532 B2 | 11/2003 | Green et al. |
| 6,656,193 B2 | 12/2003 | Grant et al. |
| 6,669,073 B2 | 12/2003 | Milliman et al. |
| 6,698,643 B2 | 3/2004 | Whitman |
| 6,716,232 B1 | 4/2004 | Vidal et al. |
| 6,722,552 B2 | 4/2004 | Fenton, Jr. |
| 6,731,473 B2 | 5/2004 | Li et al. |
| 6,755,338 B2 | 6/2004 | Hahnen et al. |
| 6,783,524 B2 | 8/2004 | Anderson et al. |
| 6,786,382 B1 | 9/2004 | Hoffman |
| 6,808,262 B2 | 10/2004 | Chapoy et al. |
| 6,830,174 B2 | 12/2004 | Hillstead et al. |
| 6,835,199 B2 | 12/2004 | McGuckin, Jr. et al. |
| 6,843,403 B2 | 1/2005 | Whitman |
| RE38,708 E | 3/2005 | Bolanos et al. |
| 6,877,647 B2 | 4/2005 | Ratcliff et al. |
| 6,879,880 B2 | 4/2005 | Nowlin et al. |
| 6,889,116 B2 | 5/2005 | Jinno |
| 6,905,057 B2 | 6/2005 | Swayze et al. |
| 6,953,138 B1 | 10/2005 | Dworak et al. |
| 6,953,139 B2 | 10/2005 | Milliman et al. |
| 6,959,852 B2 | 11/2005 | Shelton, IV et al. |
| 6,964,363 B2 | 11/2005 | Wales et al. |
| 6,978,921 B2 | 12/2005 | Shelton, IV et al. |
| 6,981,628 B2 | 1/2006 | Wales |
| 6,986,451 B1 | 1/2006 | Mastri et al. |
| 6,988,649 B2 | 1/2006 | Shelton, IV et al. |
| 6,991,627 B2 | 1/2006 | Madhani et al. |
| 7,000,818 B2 | 2/2006 | Shelton, IV et al. |
| 7,000,819 B2 | 2/2006 | Swayze et al. |
| 7,032,799 B2 | 4/2006 | Viola et al. |
| 7,044,352 B2 | 5/2006 | Shelton, IV et al. |
| 7,044,353 B2 | 5/2006 | Mastri et al. |
| 7,055,731 B2 | 6/2006 | Shelton, IV et al. |
| 7,059,508 B2 | 6/2006 | Shelton, IV et al. |
| 7,083,075 B2 | 8/2006 | Swayze et al. |
| 7,097,089 B2 | 8/2006 | Marczyk |
| 7,111,769 B2 | 9/2006 | Wales et al. |
| 7,114,642 B2 | 10/2006 | Whitman |
| 7,128,253 B2 | 10/2006 | Mastri et al. |
| 7,128,254 B2 | 10/2006 | Shelton, IV et al. |
| 7,140,528 B2 | 11/2006 | Shelton, IV |
| 7,143,923 B2 | 12/2006 | Shelton, IV et al. |
| 7,143,924 B2 | 12/2006 | Scirica et al. |
| 7,143,925 B2 | 12/2006 | Shelton, IV et al. |
| 7,147,138 B2 | 12/2006 | Shelton, IV |
| 7,159,750 B2 | 1/2007 | Racenet et al. |
| 7,543,730 B1 | 6/2009 | Marczyk |
| 2001/0041899 A1* | 11/2001 | Foster ............... 606/127 |
| 2002/0004498 A1 | 1/2002 | Doherty |
| 2002/0009193 A1 | 1/2002 | Deguchi |
| 2002/0018323 A1 | 2/2002 | Li |
| 2002/0032948 A1 | 3/2002 | Ahn |
| 2002/0036748 A1 | 3/2002 | Chapoy |
| 2002/0045442 A1 | 4/2002 | Silen et al. |
| 2002/0069565 A1 | 6/2002 | Liao |
| 2002/0084304 A1 | 7/2002 | Whitman |
| 2002/0111621 A1 | 8/2002 | Wallace et al. |
| 2002/0143346 A1 | 10/2002 | McGuckin, Jr. et al. |
| 2002/0177843 A1 | 11/2002 | Anderson et al. |
| 2002/0188294 A1 | 12/2002 | Couture |
| 2002/0190093 A1 | 12/2002 | Fenton, Jr. |
| 2003/0009193 A1 | 1/2003 | Corsaro |
| 2003/0105476 A1 | 6/2003 | Sancoff et al. |
| 2003/0132268 A1 | 7/2003 | Whitman |
| 2004/0004105 A1 | 1/2004 | Jankowski |
| 2004/0007608 A1 | 1/2004 | Ehrenfels |
| 2004/0050902 A1 | 3/2004 | Green |
| 2004/0093029 A1 | 5/2004 | Zubik et al. |
| 2004/0094597 A1 | 5/2004 | Whitman |
| 2004/0108357 A1 | 6/2004 | Milliman |
| 2004/0149802 A1 | 8/2004 | Whitman |
| 2004/0173659 A1 | 9/2004 | Green |
| 2004/0199181 A1 | 10/2004 | Knodel et al. |
| 2004/0232199 A1 | 11/2004 | Shelton, IV et al. |
| 2004/0232200 A1 | 11/2004 | Shelton, IV et al. |
| 2004/0232201 A1 | 11/2004 | Wenchell |
| 2004/0243151 A1 | 12/2004 | Demmy |
| 2004/0267310 A1 | 12/2004 | Racenet |
| 2005/0006429 A1 | 1/2005 | Wales |
| 2005/0006430 A1 | 1/2005 | Wales |
| 2005/0006431 A1 | 1/2005 | Shelton, IV et al. |
| 2005/0006432 A1 | 1/2005 | Racenet |
| 2005/0006433 A1 | 1/2005 | Milliman |
| 2005/0006434 A1 | 1/2005 | Wales et al. |
| 2005/0023324 A1 | 2/2005 | Doll et al. |
| 2005/0023325 A1 | 2/2005 | Gresham |
| 2005/0067457 A1 | 3/2005 | Shelton |
| 2005/0067458 A1 | 3/2005 | Swayze et al. |
| 2005/0067459 A1 | 3/2005 | Swayze et al. |
| 2005/0067460 A1 | 3/2005 | Milliman |
| 2005/0072827 A1 | 4/2005 | Mollenauer |
| 2005/0103819 A1 | 5/2005 | Racenet |

(56) References Cited

U.S. PATENT DOCUMENTS

| | | | |
|---|---|---|---|
| 2005/0119669 A1 | 6/2005 | Demmy | |
| 2005/0127131 A1 | 6/2005 | Mastri | |
| 2005/0165415 A1 | 7/2005 | Wales | |
| 2005/0173490 A1 | 8/2005 | Shelton, IV | |
| 2005/0178813 A1 | 8/2005 | Swayze et al. | |
| 2005/0184123 A1 | 8/2005 | Scirica et al. | |
| 2005/0184124 A1 | 8/2005 | Scirica et al. | |
| 2005/0184125 A1 | 8/2005 | Marczyk | |
| 2005/0184126 A1 | 8/2005 | Green et al. | |
| 2005/0189397 A1 | 9/2005 | Jankowski | |
| 2005/0216055 A1 | 9/2005 | Scirica et al. | |
| 2005/0228429 A1* | 10/2005 | Burgmeier et al. | 606/194 |
| 2005/0263562 A1 | 12/2005 | Shelton, IV et al. | |
| 2005/0279804 A1 | 12/2005 | Scirica et al. | |
| 2006/0000867 A1 | 1/2006 | Shelton, IV et al. | |
| 2006/0000868 A1 | 1/2006 | Shelton, IV et al. | |
| 2006/0011699 A1 | 1/2006 | Olson et al. | |
| 2006/0016853 A1 | 1/2006 | Racenet | |
| 2006/0022014 A1 | 2/2006 | Shelton, IV et al. | |
| 2006/0022015 A1 | 2/2006 | Shelton, IV et al. | |
| 2006/0049229 A1 | 3/2006 | Milliman et al. | |
| 2006/0049230 A1 | 3/2006 | Shelton, IV et al. | |
| 2006/0124688 A1 | 6/2006 | Racenet et al. | |
| 2006/0151567 A1 | 7/2006 | Roy | |
| 2006/0151568 A1 | 7/2006 | Weller et al. | |
| 2006/0175375 A1 | 8/2006 | Shelton, IV et al. | |
| 2006/0180634 A1 | 8/2006 | Shelton, IV et al. | |
| 2006/0185682 A1 | 8/2006 | Marczyk | |
| 2006/0201990 A1 | 9/2006 | Mastri et al. | |
| 2006/0201991 A1 | 9/2006 | Mastri et al. | |
| 2006/0212069 A1* | 9/2006 | Shelton | 606/205 |
| 2006/0226195 A1 | 10/2006 | Scirica et al. | |
| 2006/0226196 A1 | 10/2006 | Hueil et al. | |
| 2006/0278680 A1 | 12/2006 | Viola et al. | |
| 2006/0278681 A1 | 12/2006 | Viola et al. | |
| 2006/0289600 A1 | 12/2006 | Wales et al. | |
| 2006/0289602 A1 | 12/2006 | Wales et al. | |
| 2007/0239138 A1* | 10/2007 | Lawrence et al. | 604/531 |
| 2007/0265645 A1* | 11/2007 | Birk et al. | 606/157 |
| 2009/0076506 A1* | 3/2009 | Baker | 606/51 |

FOREIGN PATENT DOCUMENTS

| | | |
|---|---|---|
| DE | 2903159 | 1/1980 |
| DE | 3114135 | 10/1982 |
| DE | 4213426 | 10/1992 |
| DE | 4300307 | 7/1994 |
| EP | 0041022 | 12/1981 |
| EP | 0136950 | 4/1985 |
| EP | 0140552 | 5/1985 |
| EP | 0156774 | 10/1985 |
| EP | 0216532 | 4/1987 |
| EP | 0220029 | 4/1987 |
| EP | 0213817 | 11/1987 |
| EP | 0273468 | 7/1988 |
| EP | 0324166 | 7/1989 |
| EP | 0324635 | 7/1989 |
| EP | 0324637 | 7/1989 |
| EP | 0324638 | 7/1989 |
| EP | 0369324 | 5/1990 |
| EP | 0373762 | 6/1990 |
| EP | 0380025 | 8/1990 |
| EP | 0399701 | 11/1990 |
| EP | 0449394 | 10/1991 |
| EP | 0484677 | 5/1992 |
| EP | 0489436 | 6/1992 |
| EP | 0503662 | 9/1992 |
| EP | 0514139 | 11/1992 |
| EP | 0536903 | 4/1993 |
| EP | 0537572 | 4/1993 |
| EP | 0539762 | 5/1993 |
| EP | 0545029 | 6/1993 |
| EP | 0552050 | 7/1993 |
| EP | 0552423 | 7/1993 |
| EP | 0579038 | 1/1994 |
| EP | 0589306 | 3/1994 |
| EP | 0591946 | 4/1994 |
| EP | 0592243 | 4/1994 |
| EP | 0593920 | 4/1994 |
| EP | 0598202 | 5/1994 |
| EP | 0598579 | 5/1994 |
| EP | 0621006 | 10/1994 |
| EP | 0621009 | 10/1994 |
| EP | 0656188 | 6/1995 |
| EP | 0365153 | 8/1995 |
| EP | 0666057 | 8/1995 |
| EP | 0705571 | 4/1996 |
| EP | 1 563 794 A1 | 8/2005 |
| EP | 1621139 A | 2/2006 |
| EP | 1908414 A | 4/2008 |
| FR | 2542188 | 9/1984 |
| FR | 2660851 | 10/1991 |
| FR | 2681775 | 10/1991 |
| GB | 1352554 | 4/1971 |
| GB | 1452185 | 10/1976 |
| GB | 1555455 | 11/1979 |
| GB | 2048685 | 12/1980 |
| GB | 2070499 | 9/1981 |
| GB | 2141066 | 12/1984 |
| GB | 2165559 | 4/1986 |
| JP | 51-149985 | 5/1975 |
| SU | 728848 | 5/1977 |
| SU | 659146 | 4/1979 |
| SU | 980703 | 12/1982 |
| SU | 990220 | 1/1983 |
| WO | WO 89/10094 | 11/1989 |
| WO | WO9210976 | 7/1992 |
| WO | 9308754 | 5/1993 |
| WO | WO8302247 | 7/1993 |
| WO | 9314706 | 8/1993 |
| WO | WO 99/48429 A1 | 9/1999 |

OTHER PUBLICATIONS

European Search Report for EP 09252246.5-1269 date of completion is Nov. 24, 2009 (3 pages).

European Search Report for EP 07839347.7-2310 date of completion is Oct. 12, 2012 (7 pages).

* cited by examiner

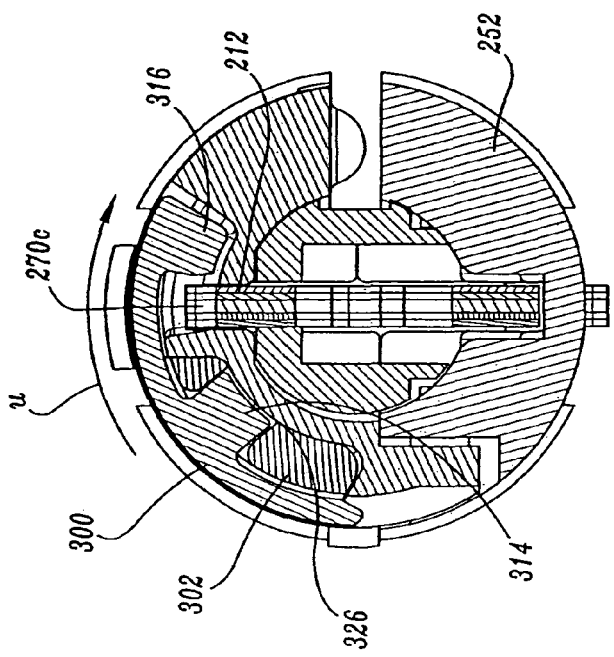
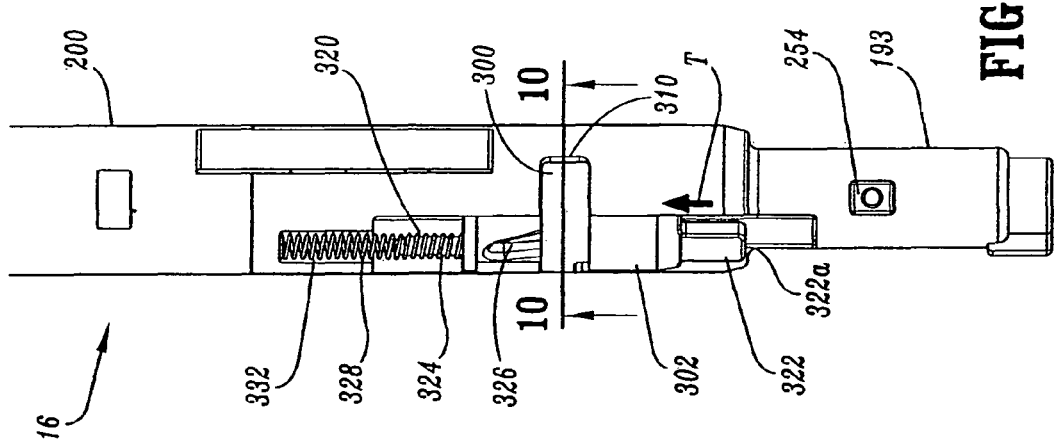
FIG. 10
FIG. 9

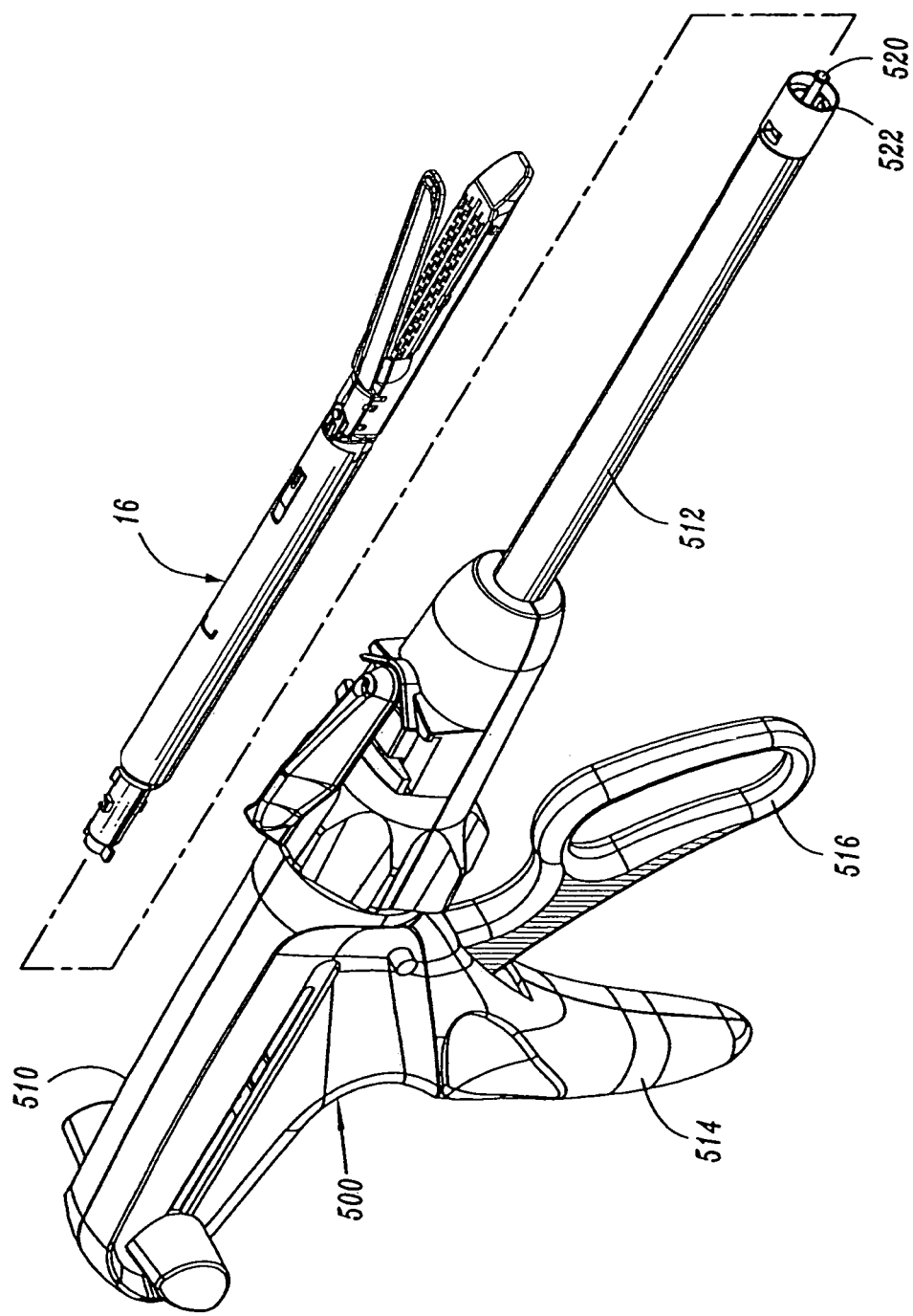

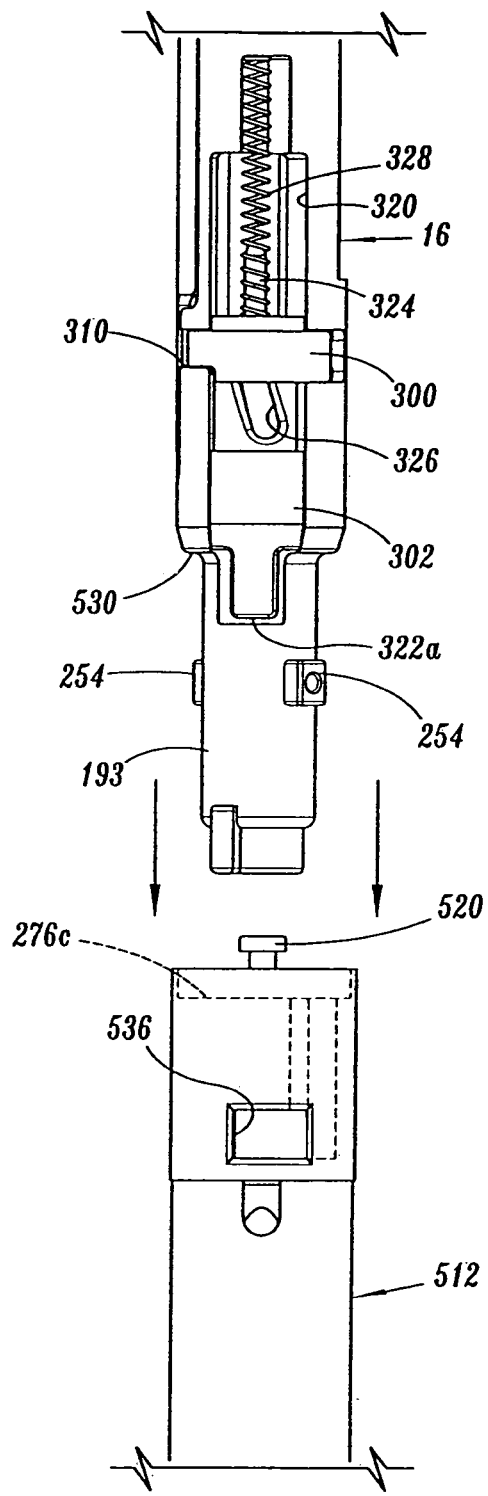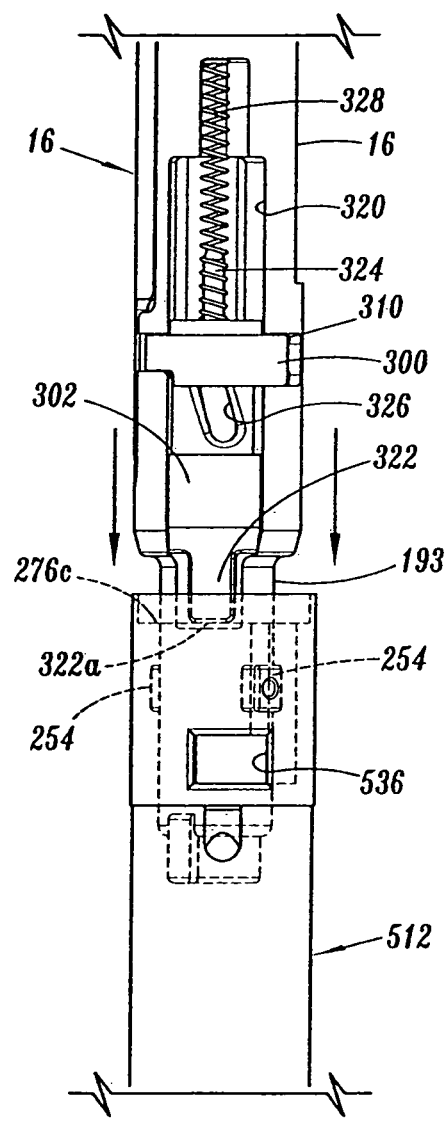
FIG. 12  FIG. 13

SURGICAL INSTRUMENT HAVING A MULTI-LAYERED DRIVE BEAM

TECHNICAL FIELD

The present disclosure relates to a surgical instrument and disposable loading unit including a plastic surface thereon. More particularly, the present disclosure relates to a surgical instrument which includes a plastic surface on at least one of a closure apparatus and a contact surface of a tool assembly.

BACKGROUND

Surgical devices wherein tissue is first grasped or clamped between opposing jaw structure and then joined by surgical fasteners are well known in the art. In some instruments, a knife is provided to cut the tissue which has been joined by the fasteners. The fasteners are typically in the form of surgical staples but two part polymeric fasteners can also be utilized.

Instruments for this purpose may include two elongated members which are respectively used to capture or clamp tissue. Typically, one of the members carries a staple cartridge that houses a plurality of staples arranged in at least two lateral rows while the other member has an anvil that defines a surface for forming the staple legs as the staples are driven from the staple cartridge. In some instruments, the closure of the two elongated members, or tool assembly, is affected by actuation of a movable handle which moves a drive beam having a closure apparatus thereon into a contact surface of a tool assembly, thus approximating the members of the tool assembly.

SUMMARY

The present disclosure relates to a surgical instrument including a handle portion, a body portion, a movable handle, a tool assembly, a drive beam and a closure apparatus. The body portion extends distally from the handle portion and defines a first longitudinal axis. The movable handle is located on the handle portion and is in mechanical cooperation with a drive member. The tool assembly is supported adjacent a distal end of the body portion and includes an anvil, a cartridge assembly and a contact surface. The drive beam includes a plurality of layers (e.g., between four, five or six) and at least one layer has a proximal engagement portion located adjacent a proximal end thereof and is configured to engage a portion of the drive member. The closure apparatus is located adjacent a distal end of the drive beam and is configured to engage the contact surface of the tool assembly and includes a cutting surface in a disclosed embodiment. At least a partial actuation of the movable handle moves the closure apparatus distally into engagement with the contact surface to approximate the anvil and the cartridge assembly. At least one of the layers (including all layers) of the drive beam is affixed to an adjacent layer of the drive beam via at least one spot weld.

In an embodiment, at least one layer (including all layers) of the drive beam is made of stainless steel. It is disclosed that all of the layers of the drive beam are affixed to each other (e.g., spot welded in at least one location). In an embodiment, the drive beam includes two outer layers and at least one inner layer; the two outer layers are affixed to the closure apparatus and to the at least one inner layer. Where there is more than one inner layer, it is disclosed that each inner layer is affixed to an adjacent inner layer in at least one location.

In an embodiment, the cross-section of the closure apparatus is generally I-shaped. It is also disclosed that each of the plurality of layers of the drive beam include a plurality of cut outs through them.

In an embodiment, the drive beam is part of a disposable loading unit. The present disclosure also relates to a disposable loading unit that includes features of the drive beam, as described above, and a tool assembly (e.g., an articulating tool assembly).

DESCRIPTION OF THE DRAWINGS

Various embodiments of the presently disclosed surgical instrument are disclosed herein with reference to the drawings, wherein:

FIG. 9 is a top view of the proximal end of the DLU proximal body portion shown in FIG. 1A with the locking mechanism in its unlocked position;

FIG. 10 is a cross-sectional view taken along section lines 10-10 of FIG. 9;

FIG. 11 is a side perspective view of the DLU and surgical instrument shown in FIG. 1 prior to attachment of the DLU to the surgical instrument;

FIG. 12 is a top view of the proximal end of the DLU and the distal end of the surgical instrument shown in FIG. 11 prior to attachment to the distal end of the surgical instrument;

FIG. 13 is a top view of the proximal end of the DLU shown in FIG. 11 as the DLU is advanced linearly into the distal end of the surgical instrument;

DETAILED DESCRIPTION OF EMBODIMENTS

Figure 1:
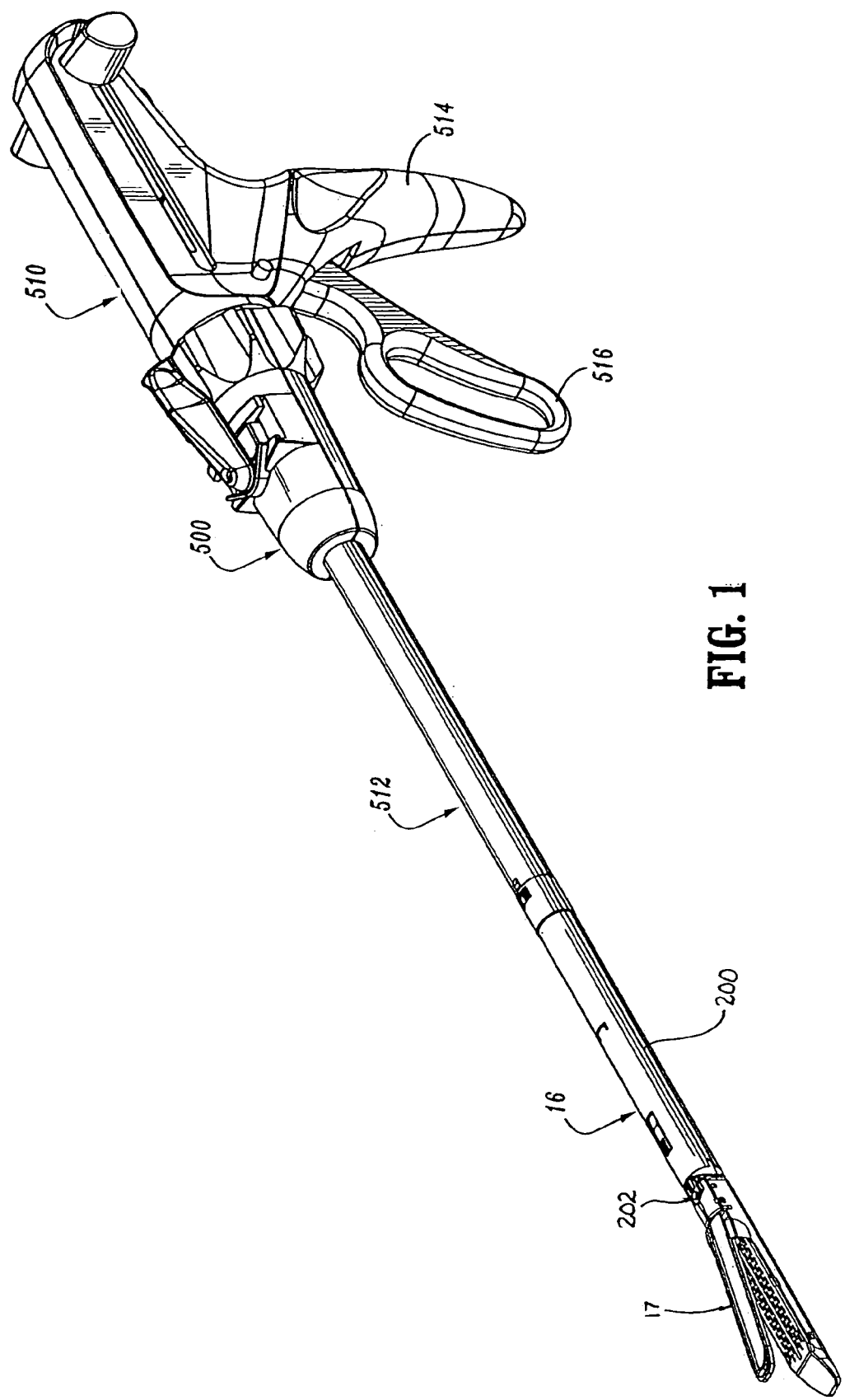
FIG. 1 is a side perspective view from the distal end of one embodiment of the presently disclosed surgical instrument with articulating tool assembly.

Embodiments of the presently disclosed surgical instrument and DLU will now be described in detail with reference to the drawings, in which like reference numerals designate identical or corresponding elements in each of the several views.

Referring to FIG. 1, surgical instrument 500 includes a handle portion 510, a body portion 512, and a disposable loading unit ("DLU") 16. Handle portion 510 includes a stationary handle 514 and a movable handle or trigger 516. Movable handle 516 is movable in relation to stationary handle 514 to advance a control rod 520 which projects from the distal end of body portion 512. Handle portion 510 and body portion 512 may be constructed in the manner disclosed in U.S. Pat. No. 6,330,965 which is hereby incorporated herein in its entirety by reference. Alternately, other surgical instruments can be used with DLU 16 to perform endoscopic surgical procedures.

Figure 1A:
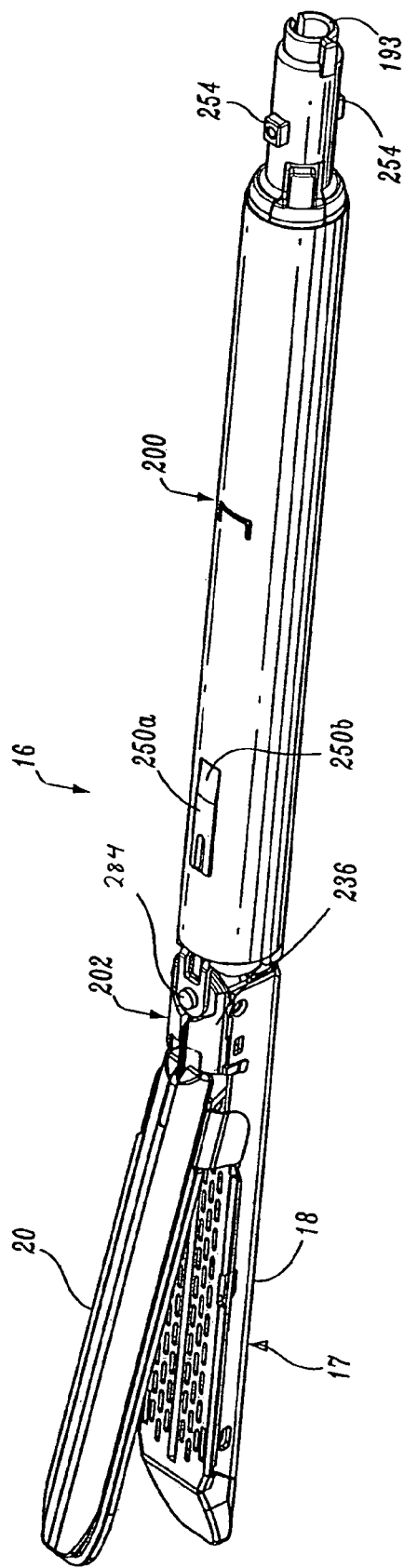
FIG. 1A is a side perspective view from the proximal end of a disposable loading unit (DLU) of the surgical instrument shown in FIG. 1 including the tool assembly.

Referring to FIGS. 1 and 1A, briefly, DLU 16 includes a tool assembly 17, a proximal body portion 200 and a mounting assembly 202. Body portion 200 has a proximal end adapted to releasably engage the distal end of a surgical instrument 500 (FIG. 11) in the manner to be discussed in detail below. Mounting assembly 202 is pivotally secured to a distal end of body portion 200 and is fixedly secured to a proximal end of tool assembly 17. Pivotal movement of mounting assembly 202 about an axis perpendicular to a longitudinal axis of body portion 200 affects articulation of tool assembly 17 between a non-articulated position in which the longitudinal axis of tool assembly 17 is aligned with the longitudinal axis of body portion 200 and an articulated position in which the longitudinal axis of tool assembly 17 is disposed at an angle to the longitudinal axis of body portion 200.

Figure 2:
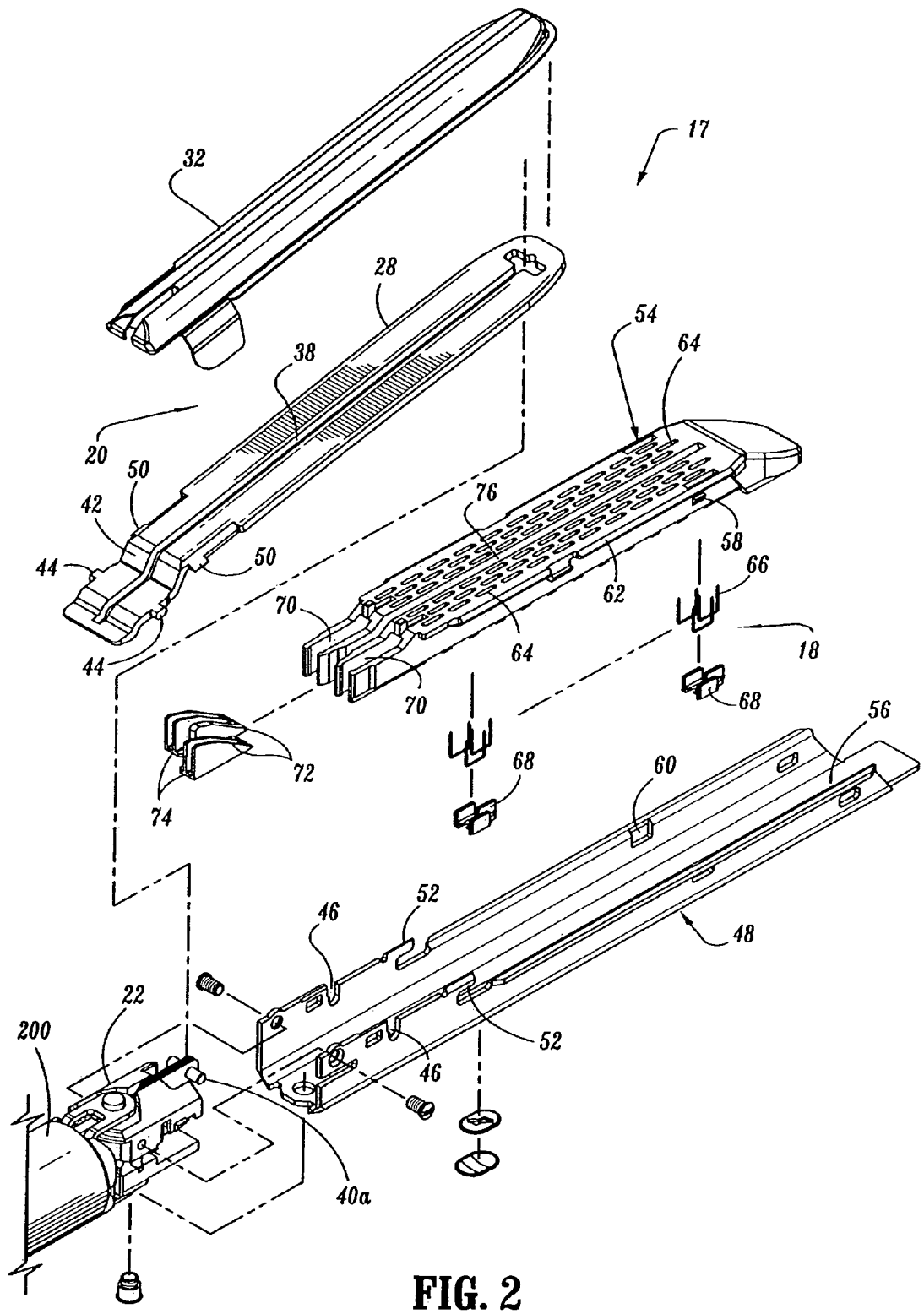
FIG. 2 is a side perspective view of the distal end of mounting assembly and tool assembly, with parts separated, of the DLU of the surgical instrument shown in FIG. 1.
Figure 3:
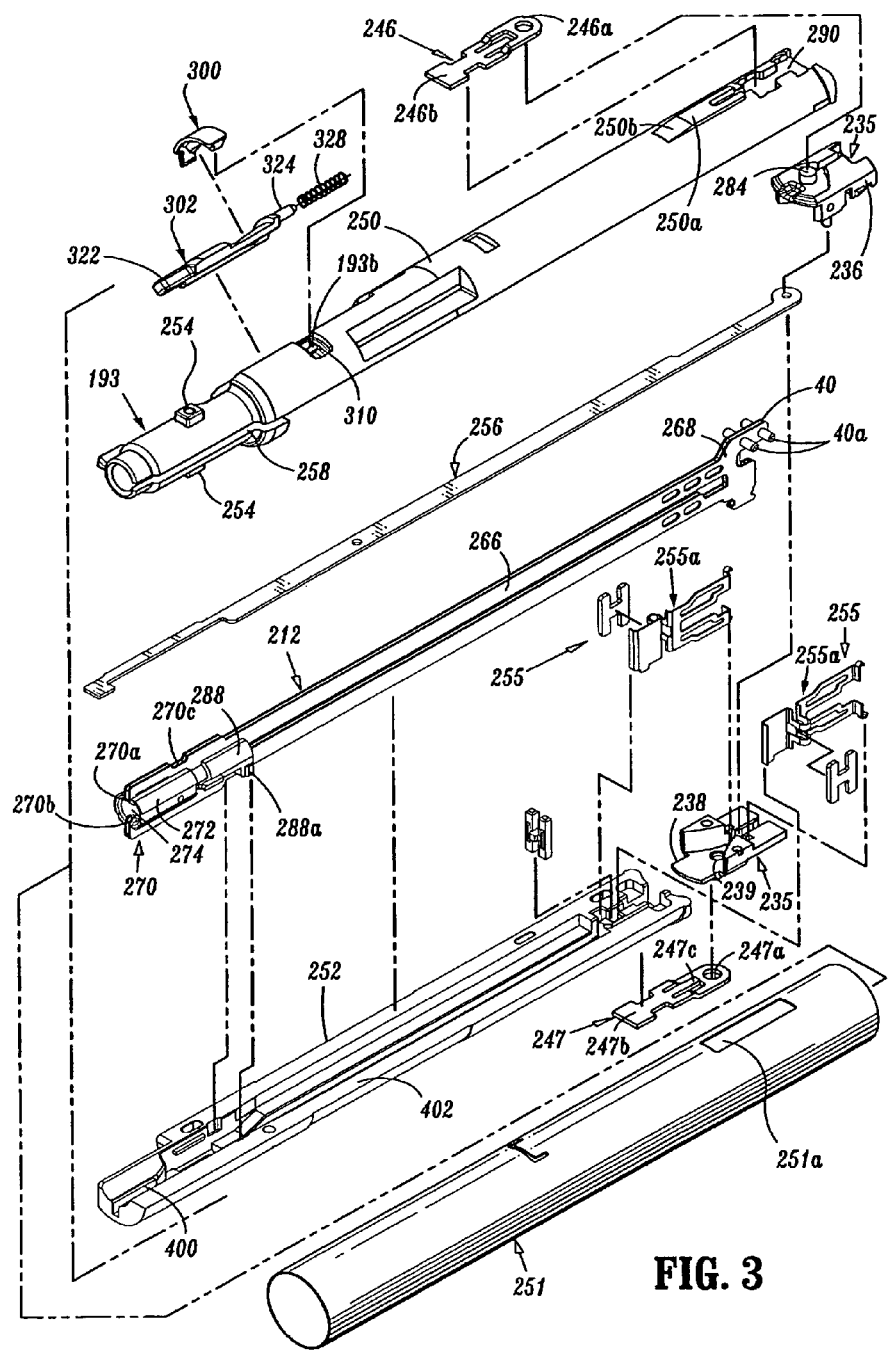
FIG. 3 is a side perspective view of the mounting assembly and the proximal body portion of the DLU shown in FIG. 1A with parts separated.
Figure 4:
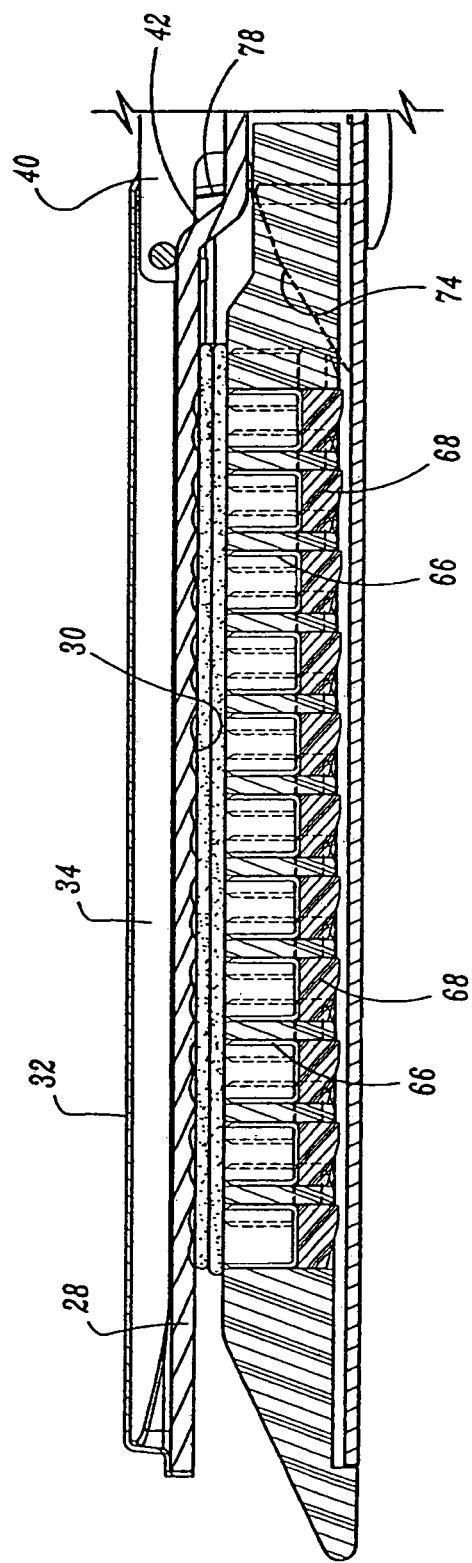
FIG. 4 is a side cross-sectional view of the tool assembly of the DLU shown in FIG. 1A.

Referring to FIGS. 2-4, tool assembly 17 includes a cartridge assembly 18 and an anvil assembly 20. Anvil assembly 20 includes an anvil portion 28 having a plurality of staple deforming concavities 30 (FIG. 4) and a cover plate 32 secured to a top surface of anvil portion 28. Cover plate 32 and anvil portion 28 define a cavity 34 (FIG. 4) therebetween which is dimensioned to receive a distal end of a drive assembly 212 (FIG. 3). Cover plate 32 encloses the distal end of drive assembly 212 to prevent pinching of tissue during actuation of DLU 16. A longitudinal slot 38 extends through anvil portion 28 to facilitate passage of a retention flange 40 of drive assembly 212. A camming surface 42 formed on anvil portion 28 is positioned to engage a pair of cam members 40a supported on retention flange 40 of drive assembly 212 to effect approximation of the anvil and cartridge assemblies. A pair of pivot members 44 are formed. A pair of stabilizing members 50 engage a respective shoulder 52 formed on carrier 48 to prevent anvil portion 28 from sliding axially in relation to staple cartridge 54 as camming surface 42 is pivoted about pivot members 44.

Cartridge assembly 18 includes carrier 48 which defines an elongated support channel 56 which is dimensioned and configured to receive staple cartridge 54. Corresponding tabs 58 and slots 60 formed along staple cartridge 54 and elongated support channel 56, respectively, function to retain staple cartridge 54 at a fixed location within support channel 56. A pair of support struts 62 formed on staple cartridge 54 are positioned to rest on side walls of carrier 48 to further stabilize staple cartridge 54 within support channel 56. Carrier 48 has slots 46 for receiving pivot members 44 of anvil portion 28 and allowing anvil portion 28 to move between spaced and approximated positions.

Staple cartridge 54 includes retention slots 64 (FIG. 2) for receiving a plurality of staples or fasteners 66 and pushers 68. A plurality of laterally spaced apart longitudinal slots 70 extend through staple cartridge 54 to accommodate upstanding cam wedges 72 of an actuation sled 74 (FIG. 2). A central longitudinal slot 76 extends along substantially the length of staple cartridge 54 to facilitate passage of a knife blade 78 (FIG. 4). During operation of surgical stapler 10, drive assembly 212 abuts actuation sled 74 and pushes actuation sled 74 through longitudinal slots 70 of staple cartridge 54 to advance cam wedges 72 into sequential contact with pushers 68. Pushers 68 translate vertically along cam wedges 72 within fastener retention slots 64 and urge fasteners 66 from retention slots 64 into staple deforming cavities 30 (FIG. 4) of anvil assembly 20.

Referring to FIG. 3, mounting assembly 235 includes an upper mounting portion 236 and a lower mounting portion 238. A centrally located pivot member 284 extends from upper mounting portion 236 through a respective opening 246a formed in a first coupling member 246. Lower mounting portion 238 includes a bore 239 for receiving pivot member 284 (see FIG. 3F). Pivot member 284 extends through bore 239 and opening 247a of a second coupling member 247. Each of coupling members 246, 247 includes an interlocking proximal portion 246b, 247b configured to be received in grooves 290 formed in the distal end of an inner housing which is formed from upper and lower housing halves 250 and 252. Coupling members 246, 247 retain mounting assembly 235 and upper and lower housing halves 250 and 252 in a longitudinally fixed position in relation to each other while permitting pivotal movement of mounting assembly 235 in relation thereto.

Figure 3A:
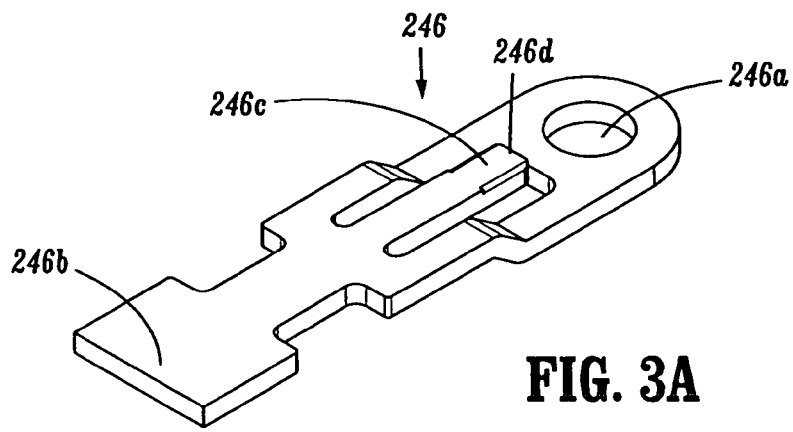
FIG. 3A is a side perspective view of a coupling member of the surgical instrument shown in FIG. 1.
Figure 3B:
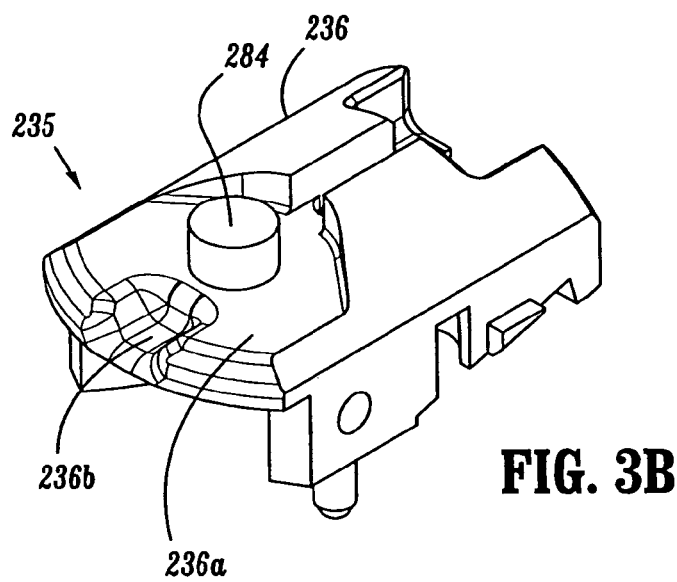
FIG. 3B is a side perspective view of an upper mounting portion of the mounting assembly of the DLU of the surgical instrument shown in FIG. 1.
Figure 3C:
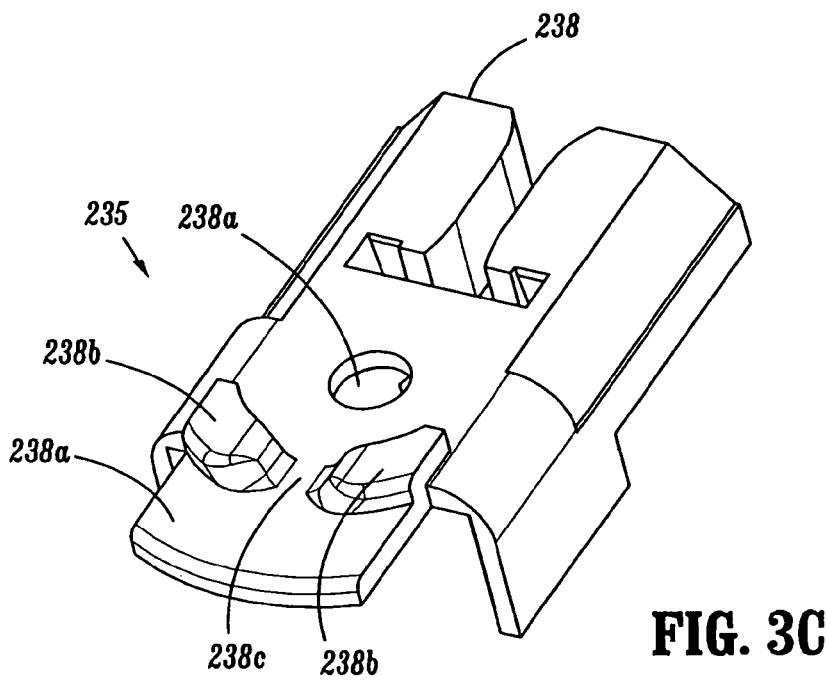
FIG. 3C is a side perspective view of a lower mounting portion of the mounting assembly of the DLU of the surgical instrument shown in FIG. 1.
Figure 3D:
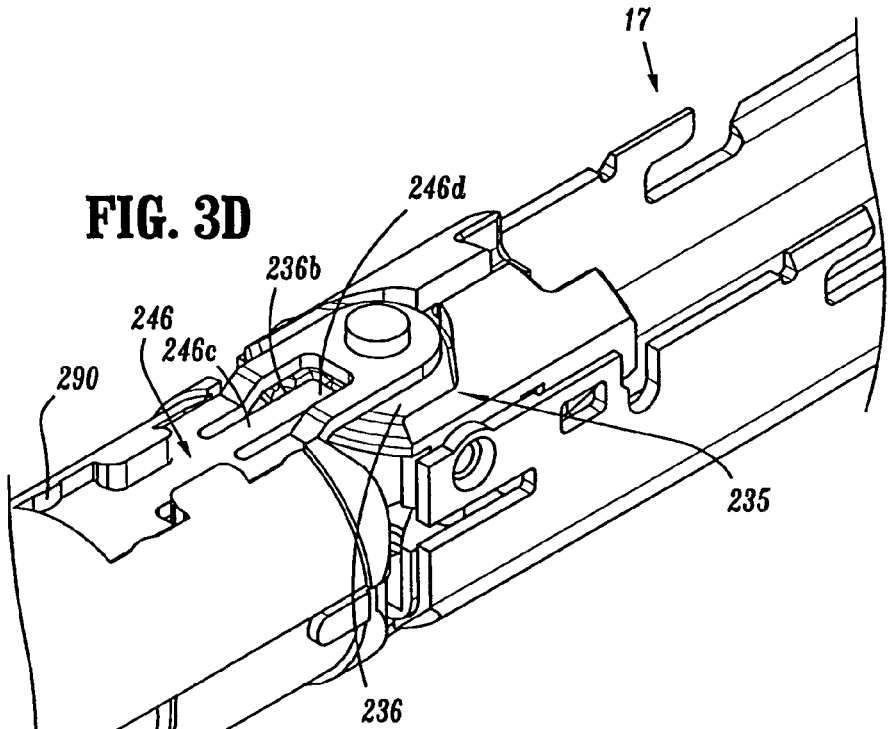
FIG. 3D is a side perspective view from above the proximal body portion, the mounting assembly and the tool assembly of the DLU of the surgical instrument with the tool assembly in its non-articulated position.

Referring to FIGS. 3A-3C, each coupling member 246, 247 includes a cantilevered spring arm 246c which has a distal end 246d positioned to engage mounting assembly 235. More specifically, upper mounting portion 236 includes a top surface 236a which includes a recess 236b dimensioned to receive distal end 246d of spring arm 246c of a respective coupling member 246. Lower mounting portion 238 includes a bottom surface 238a having a pair of raised surfaces 238b which define a recess 238c which is dimensioned to receive spring arm 247c of a respective coupling member 247. Alternatively, at least one recess may be formed in the proximal end of tool assembly 17.

Figure 3E:
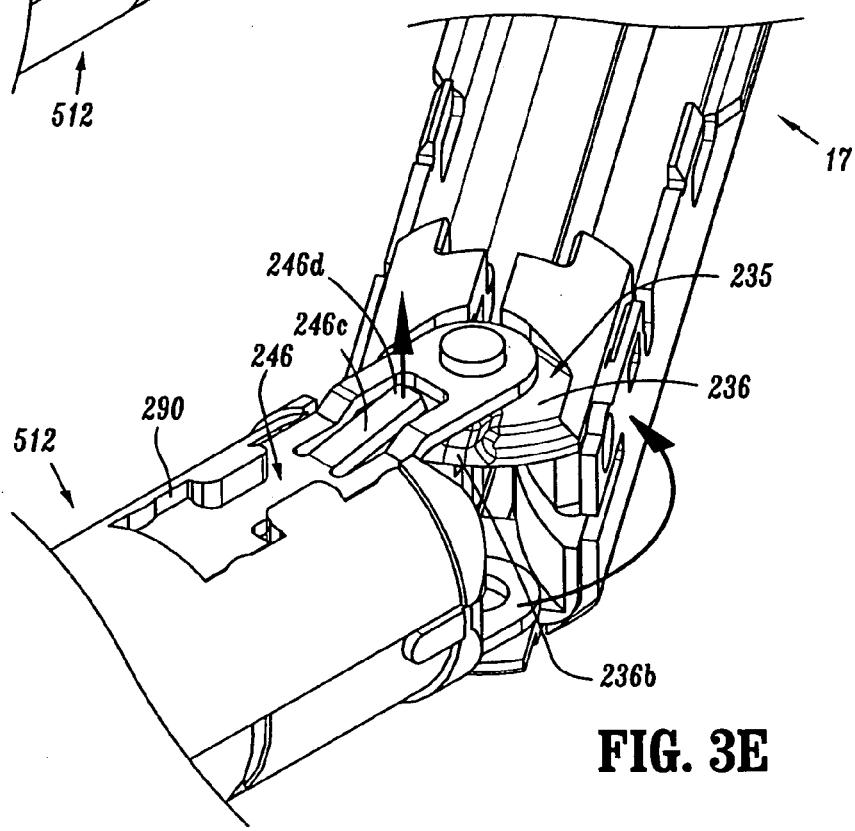
FIG. 3E is a side perspective view from above the proximal body portion, the mounting assembly and the tool assembly shown in FIG. 3D with the tool assembly in an articulated position.
Figure 3F:
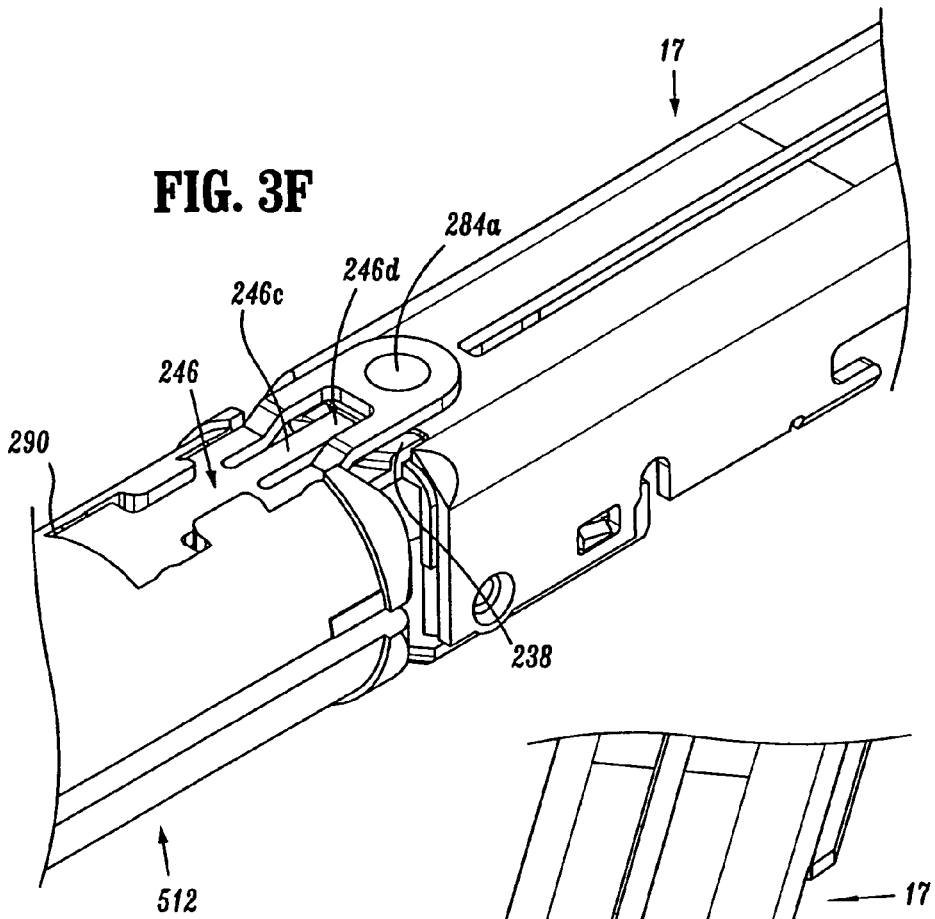
FIG. 3F is a side perspective view from below the proximal body portion, the mounting assembly and the tool assembly of the DLU of the surgical instrument with the tool assembly in its non-articulated position.
Figure 3G:
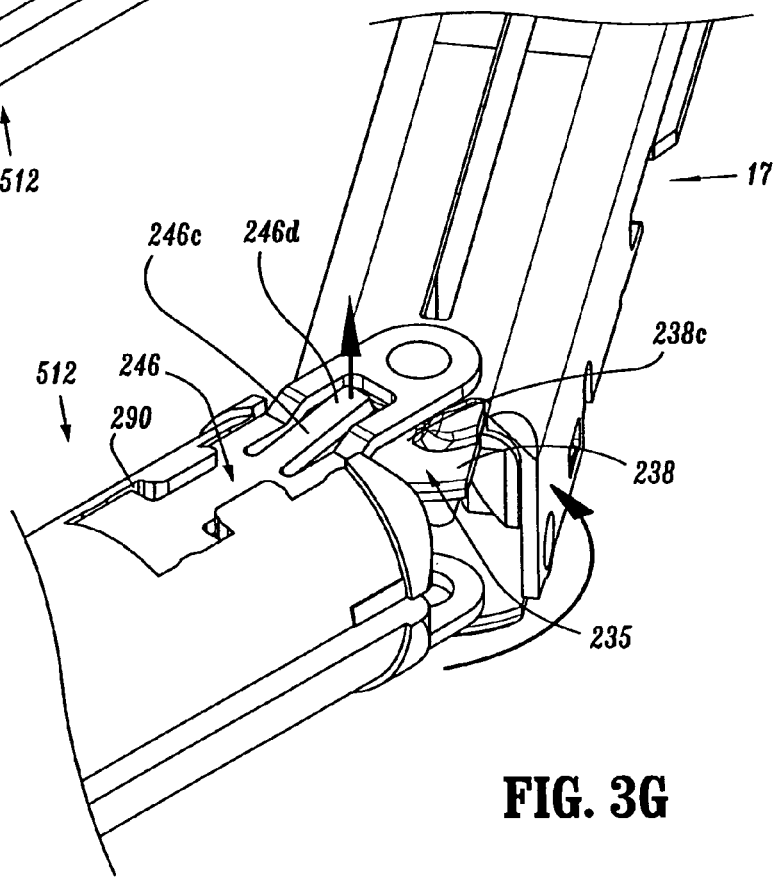
FIG. 3G is a side perspective view from below the proximal body portion, the mounting assembly and the tool assembly shown in FIG. 3F with the tool assembly in an articulated position.

As illustrated in FIGS. 3D-3G, when distal end of spring arms 246c, 247c of coupling members 246, 247 are positioned in recesses 236b and 238c of upper and lower mounting portions 236 and 238, respectively, spring arms 246c, 247c retain mounting assembly 235 in a non-articulated position. Spring arms 246c, 247c will retain mounting assembly 235 in its non-articulated position until a predetermined force sufficient to deflect spring arms 246c from recesses 236b and 238c is applied to effect articulation of mounting assembly 235 and tool assembly 17. When the predetermined force is applied to the mounting assembly 235 and tool assembly 17, spring arms 246c, 247c will spring or deflect outwardly from recesses 236b and 238c, as shown in FIGS. 3E and 3G, to permit pivotal movement of mounting assembly 235 (and, thus, tool assembly 17) in relation to the distal end of proximal body portion 200 of the DLU 16.

As discussed above, spring arms 246c and recesses 236b and 238c maintain tool assembly 17 in its non-articulated position until a predetermined force has been applied to mounting assembly 235 to disengage spring arms 246c, 247c from recesses 236b and 238c of mounting assembly 235. It is envisioned that the spring arms/recesses could be incorporated into any articulating surgical device including staplers, graspers (See FIG. 3H), powered sealing devices, e.g., RF sealing devices, etc. Further, although two spring arms/recesses are shown, a single spring arm can be provided. Moreover, the articulating tool assembly need not form part of a DLU but rather can be supported directly on the distal end of a surgical instrument. For example, the mounting assembly can be removably or irremovably secured to the tool assembly and secured directly to the distal end of a surgical instrument.

Upper housing half 250 and lower housing half 252 are contained within an outer sleeve 251 of body portion 200 (FIG. 3). Body portion 200 includes a cutout 251a dimensioned to receive a boss or projection 250a formed on upper housing half 250. The positioning of projection 250a within cutout 251a prevents axial and rotational movement of upper and lower housing halves 250 and 252 within outer sleeve 251 of body portion 200. In one embodiment, boss 250a has a substantially rectangular configuration having a greater axial dimension than lateral dimension. The greater axial dimension provides increased surface area for preventing rotation of upper and lower housing halves 250 and 252 within sleeve 251. A proximal portion 250b of boss 250a is ramped. Ramped proximal portion 250b allows sleeve 251 to be slid over boss 250a as upper and lower housing halves 250 and 252 are positioned within sleeve 251. It is envisioned that boss 250a may assume other configurations, e.g., circular, square, triangular, etc., and still achieve its intended function. Further, boss 250a can be repositioned anywhere along upper housing half 250 or, in the alternative, be positioned on lower housing half 252 or partly on each housing half 250 and 252.

Figure 7:
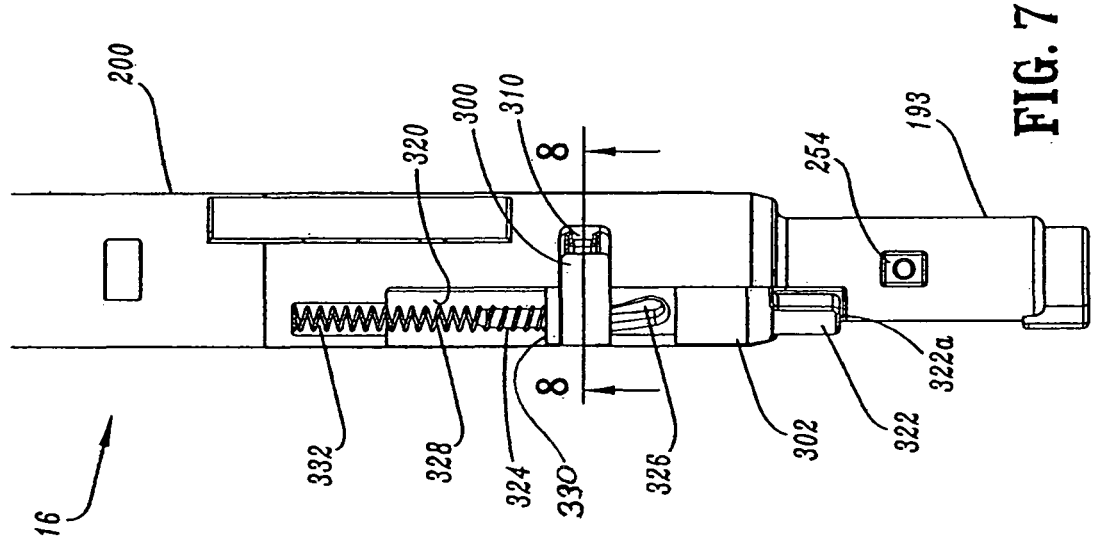
FIG. 7 is a top view of the proximal end of the DLU proximal body portion shown in FIG. 1A with the locking mechanism in its locked position.
Figure 14:
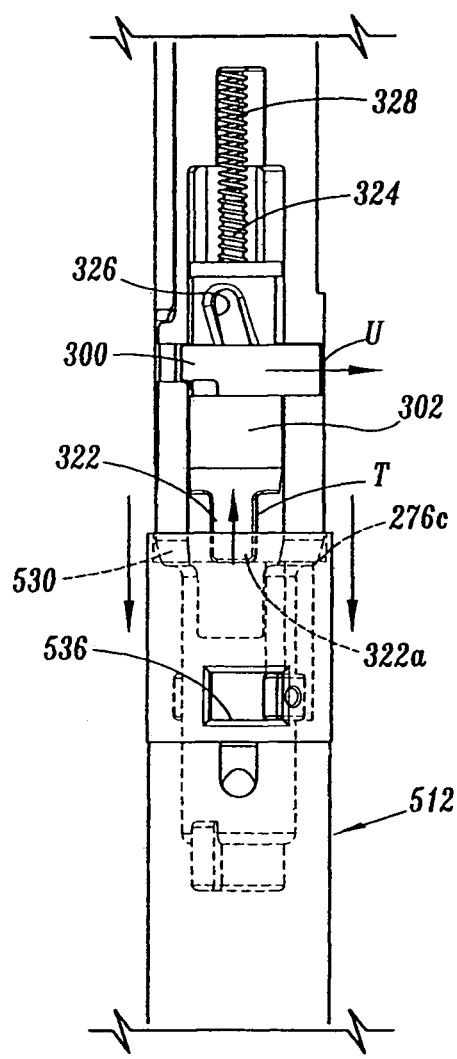
FIG. 14 is a top view of the proximal end of the DLU and the distal end of the surgical instrument shown in FIG. 12 after the DLU has been advanced linearly but prior to locking the DLU to the surgical instrument.
Figure 15:
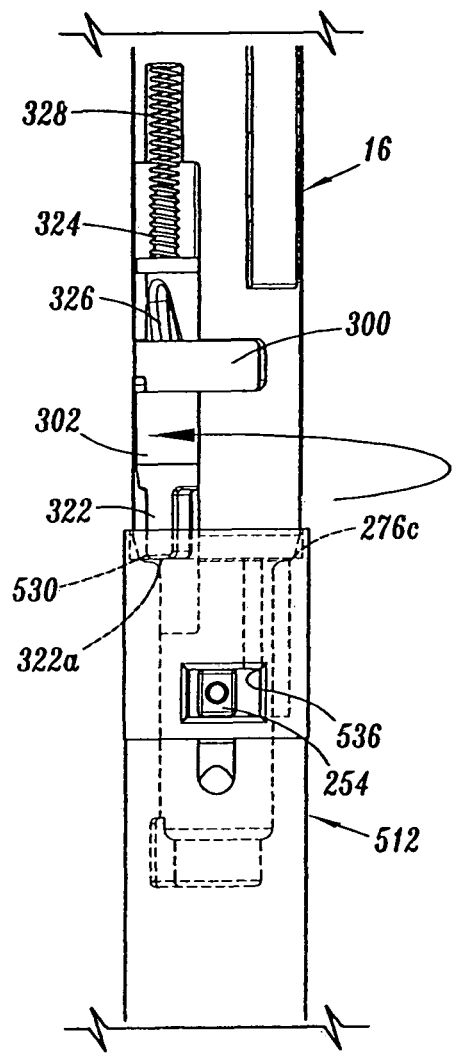
FIG. 15 is a top view of the proximal end of the DLU and the distal end of the surgical instrument shown in FIG. 13 after the DLU has been advanced linearly and rotatably locked onto the surgical instrument.

The proximal end or insertion tip 193 of upper housing half 250 includes engagement nubs 254 for releasably engaging the distal end of a surgical instrument in a bayonet-type fashion (see FIGS. 1A and 7). Housing halves 250 and 252 define a channel 400 for slidably receiving axial drive assembly 212 therein. An articulation link 256 is dimensioned to be slidably positioned within a slot 402 formed between upper and lower housing halves 250 and 252. A pair of H-block assemblies 255 are positioned adjacent the distal end of housing portion 200 and adjacent the distal end of axial drive assembly 212 to prevent outward buckling and bulging of drive assembly 212 during articulation and firing of surgical stapling apparatus 10. Each H-block assembly 255 includes a flexible body 255a which includes a proximal end fixedly secured to body portion 200 and a distal end fixedly secured to mounting assembly 235 (FIG. 3).

A retention member 288 is supported on engagement section 270 of axial drive assembly 212. Retention member 288 includes a pair of fingers 288a which are releasably positioned within slots or recesses 252a formed in lower housing half 252. In operation, when SULU 16 is attached to a surgical instrument and axial drive assembly 212 is actuated by applying a predetermined force to an actuation member 516 of the surgical instrument 500 (FIG. 11), axial drive assembly 212 is advanced distally to move drive assembly 212 and retention member 288 distally. As retention member 288 is advanced distally, fingers 288a are forced from recesses 252a to provide an audible and tactile indication that the surgical instrument has been actuated. Retention member 288 is designed to prevent inadvertent partial actuation of DLU 16, such as during shipping, by maintaining axial drive assembly 212 at a fixed position within DLU 16 until a predetermined axial force has been applied to axial drive assembly 212.

Axial drive assembly 212 includes an elongated drive beam 266 including a distal working head 268 and a proximal engagement section 270. In one embodiment, drive beam 266 is constructed from multiple stacked sheets of material. Engagement section 270 includes a pair of resilient engagement fingers 270a and 270b which mountingly engage a pair of corresponding retention slots formed in drive member 272. Drive member 272 includes a proximal porthole 274 configured to receive distal end of a control rod 520 (FIG. 11) of a surgical instrument when the proximal end of DLU 16 is engaged with the body portion 512 of a surgical instrument 500.

Referring also to FIGS. 5-10, DLU 16 further includes a locking mechanism including a locking member 300 and a locking member actuator 302. Locking member 300 (FIG. 6) is rotatably supported within a longitudinal or axial slot 310 (FIG. 7) formed in a proximal portion of upper housing half 250 of body portion 200 of DLU 16. Locking member 300 is movable from a first position (FIGS. 7 and 8), in which locking member 300 maintains drive assembly 212 in a pre-fired position, to a second position (FIGS. 9 and 10), in which drive assembly 212 is free to move axially.

Figure 6:
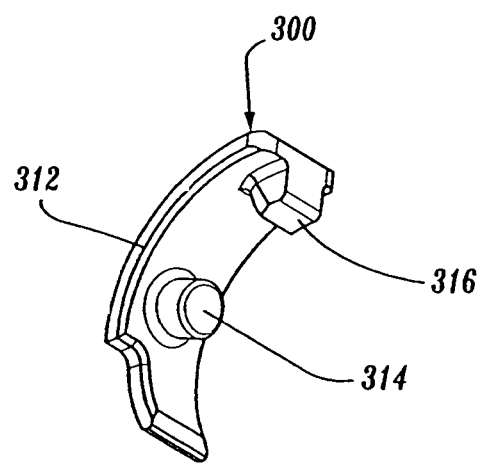
FIG. 6 is a bottom perspective view of a locking member of the locking mechanism shown in FIG. 3.
Figure 8:
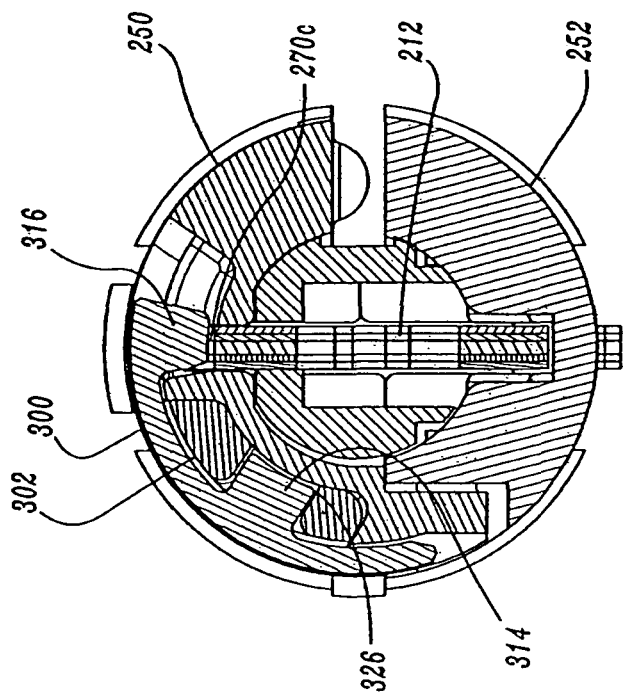
FIG. 8 is a cross-sectional view taken along section lines 8-8 of FIG. 7.

As illustrated in FIG. 6, locking member 300 includes semi-cylindrical body 312 which is slidably positioned within transverse slot 310 formed in upper housing half 250 of body portion 200. Body 312 includes a radially inwardly extending cam member 314 and a radially inwardly extending finger 316. Finger 316 is dimensioned to be slidably received within a notch or slot 270c (FIG. 3) formed in drive assembly 212. Engagement of finger 316 in notch 270c of drive assembly 212 prevents drive assembly 212 from moving linearly within body portion 200 and, thus, prevents actuation of DLU 16.

Figure 5:
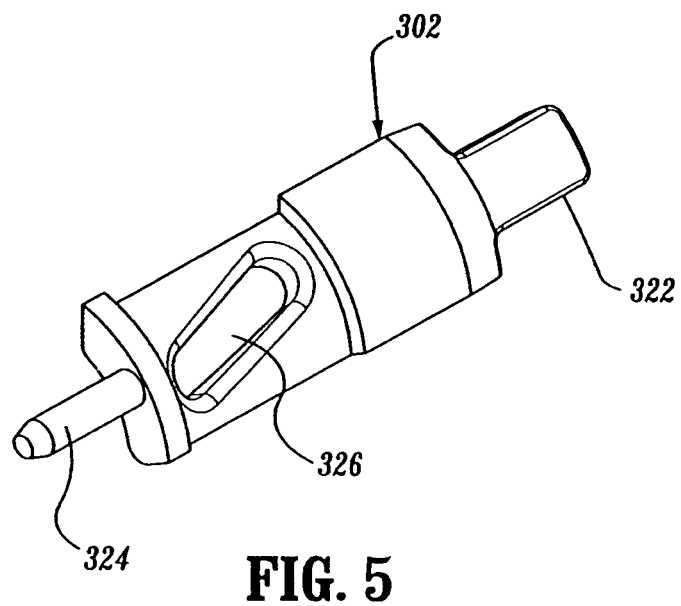
FIG. 5 is a top perspective view of the lock member actuator of the proximal body portion locking mechanism shown in FIG. 3.

Referring to FIGS. 3, 5 and 7, a locking member actuator 302 is slidably positioned within a axial slot 320 (FIG. 7) formed in upper housing half 250 of body portion 200 of DLU 16. Actuator 302 includes a proximal abutment member 322, a distal spring guide 324, and a central cam slot 326. Axial slot 320 intersects transverse slot 310 such that cam member 314 of locking member 300 is slidably positioned within cam slot 326 of locking member actuator 302. A biasing member or spring 328 (FIG. 7) is positioned about spring guide 324 between a distal surface 330 of actuator 302 and a wall 332 (FIG. 7) defining the distal end of axial slot 320. Spring 328 urges actuator 302 to its retracted position within axial slot 320. In its retracted position, abutment member 322 is positioned on and extends radially outwardly of the proximal end of DLU 16 adjacent insertion tip 193 of proximal body portion 200 and cam slot 326 is positioned to locate cam member 314 such that finger 316 of lock member 300 is positioned within notch 270c of drive assembly 212.

FIGS. 11-15 illustrate DLU 16 and surgical instrument 500 prior to and during attachment of DLU 16 to surgical instrument 500. Prior to attachment of DLU 16 onto surgical instrument 500, spring 328 urges actuator 302 to its retracted position to move lock member 300 to its locked position as discussed above. When insertion tip 193 DLU 16 is linearly inserted into the open end 522 (FIG. 11) of the body portion 512 (FIG. 13) of a surgical instrument 500, nubs 254 move linearly through slots (not shown) formed in open end 522 of body portion 512. As nubs 254 pass through the slots, the proximal end 322a of abutment member 322, which is angularly offset from nubs 254, abuts a wall 276c defining the slots for receiving nubs 254. As DLU 16 is moved further into body portion 512, locking member actuator 302 is moved from its retracted position to its advanced position in the direction indicated by arrow "T" in FIG. 14. As actuator 302 is moved to its advanced position, lock member 300 is cammed in the direction indicated by arrow "U" in FIG. 14 from its locked position (FIG. 8) engaged with drive assembly 212 to its unlocked position (FIG. 10) to move finger 316 from notch 270c. The locking mechanism including locking member 300 and locking member actuator 302 prevents accidental or inadvertent advancement or manipulation of the drive member of DLU 16 such as during loading of DLU 16 onto a surgical instrument 500.

When DLU 16 has been moved linearly in relation to instrument 500 to a position wherein a proximal surface 530 of body portion 200 abuts inner surface 276c of body portion 512 (FIG. 15), DLU 16 can be rotated in relation to body portion 512 in a bayonet-type action to position nubs 254 within openings 536 of body portion 512 to lock DLU 16 onto body portion 512. It is envisioned that other coupling types besides bayonet couplings may be used to connect DLU 16 to instrument 500, e.g., spring detent or snap-fit couplings, friction fit couplings, interlocking members, threaded couplings etc.

In an embodiment of the present disclosure illustrated in FIGS. 16-20, a locking assembly 600 is illustrated for use with surgical instrument 500 and disposable loading unit 16 (see FIG. 1, for example). In the illustrated embodiments, locking assembly 600 includes a housing 602, a pusher 604, a rod 606, a slide 608, at least one spring 610, a cam finger 612, a pivot plate 614 having slots 616 and a link 618. Locking assembly 600 generally helps tool assembly 17 (see FIG. 1, for example) maintain its position during firing of surgical instrument 500.

Figure 16:
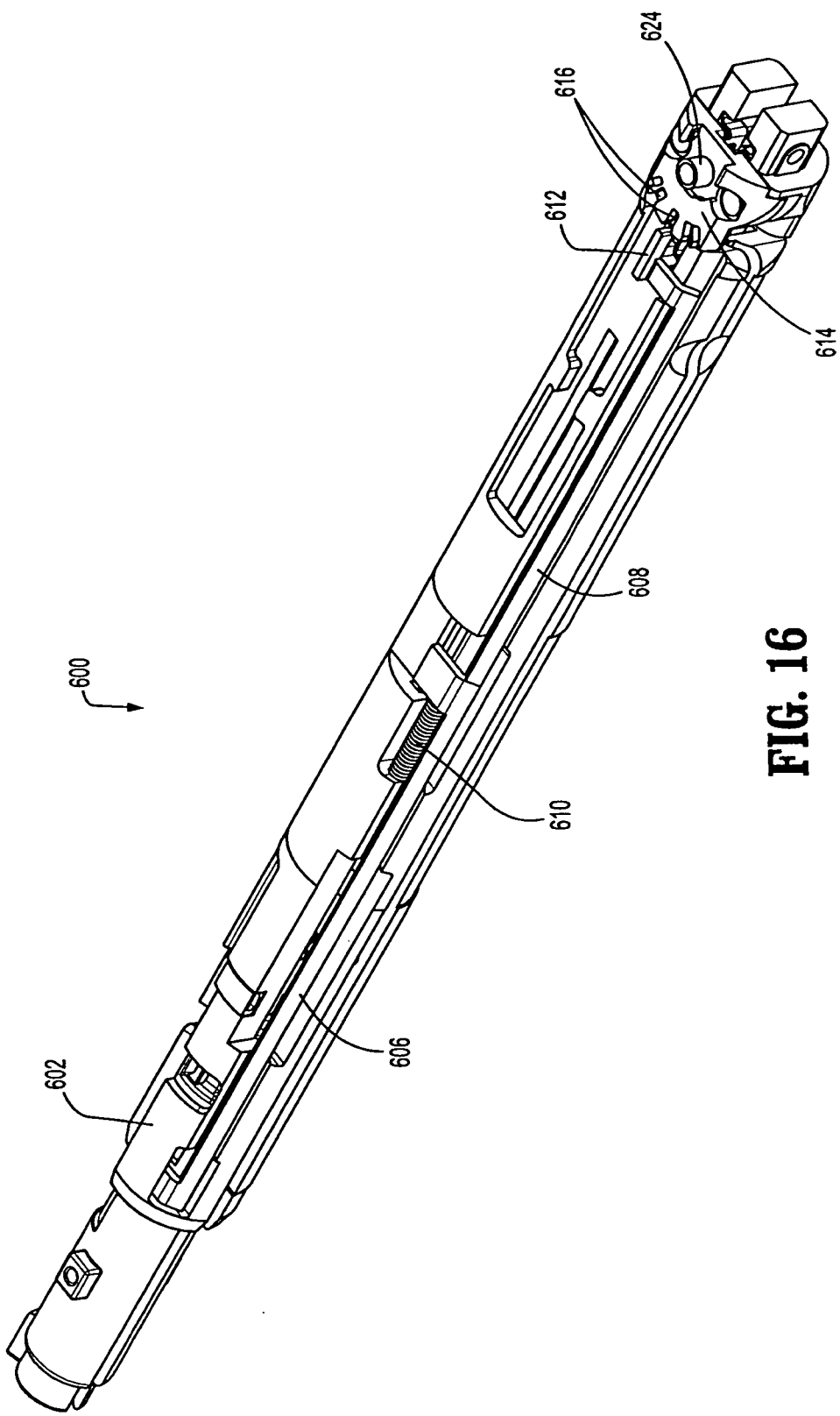
FIG. 16 is a perspective view of a locking assembly for use with a surgical instrument in accordance with an embodiment of the present disclosure.
Figure 17:
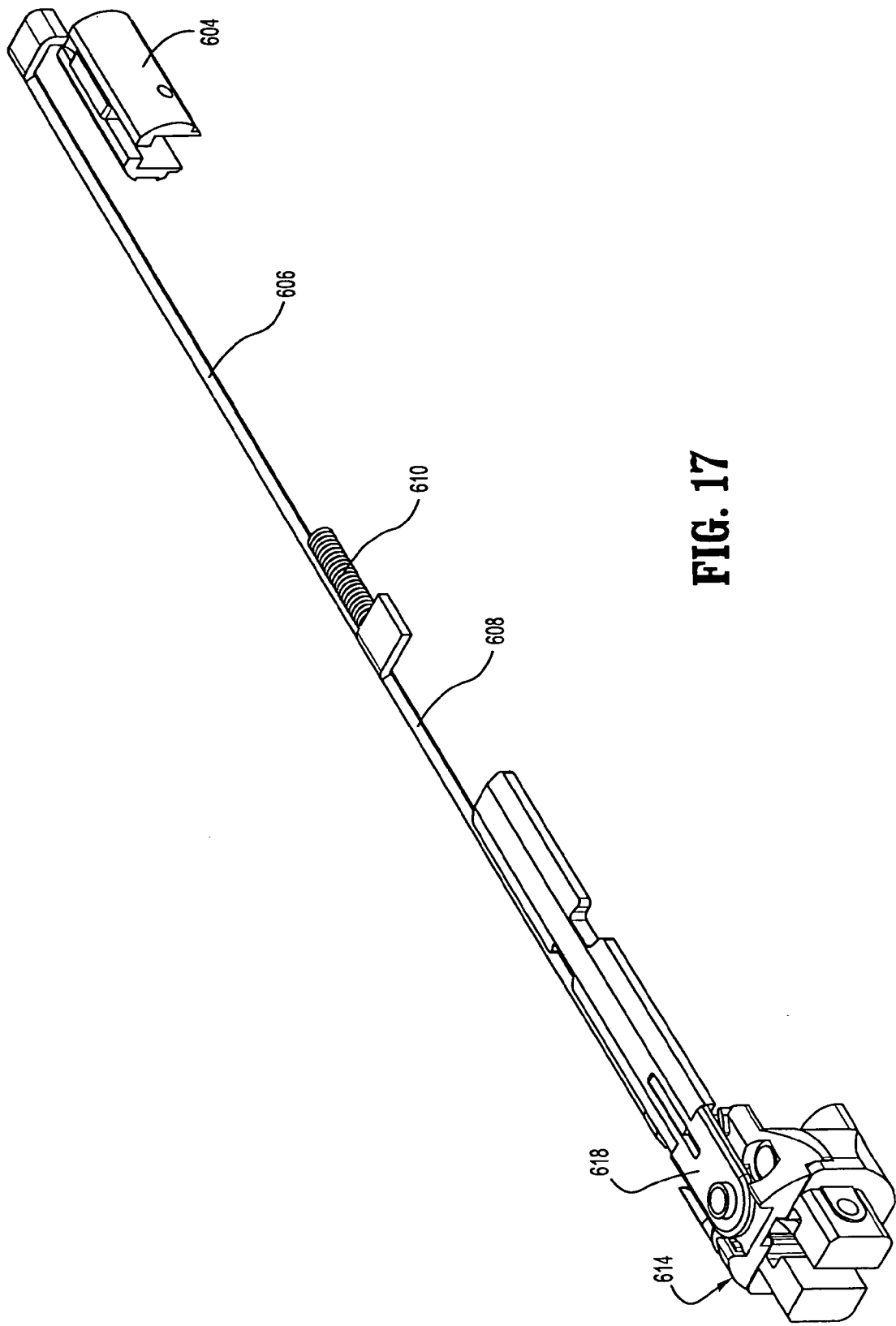
FIG. 17 is a perspective view of various components of the locking assembly of FIG. 16.

Referring to FIGS. 16 and 17, a portion of locking assembly 600 is at least partially contained within a housing 602. FIG. 16 illustrates locking assembly 600 disposed in relation to housing 602, while FIG. 17 illustrates locking assembly 600 isolated from housing 602. In the illustrated embodiment of FIG. 17, pusher 604 is shown with rod 606 extending distally therefrom. Slide 608 extends distally from rod 606 and is in a slidable relationship therewith, thus allowing slide 608 to move axially with respect to rod 606. Spring 610 or pair of springs (not explicitly shown in this embodiment) distally biases slide 608 from rod 606.

Figure 18:
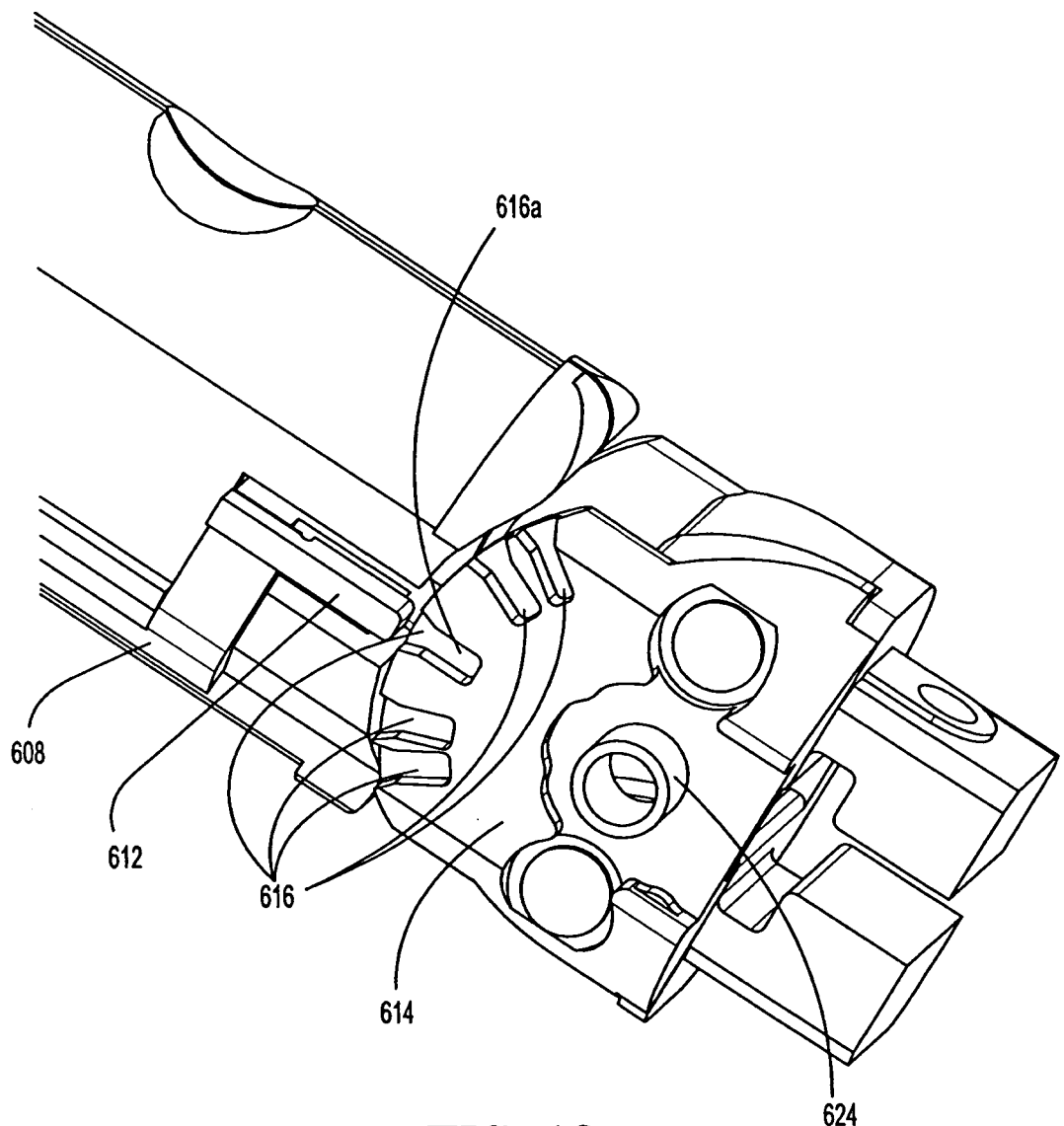
FIG. 18 is an enlarged perspective view of a portion of the locking assembly of FIGS. 16 and 17 illustrated with the articulating tool assembly in a non-articulated position.
Figure 19:
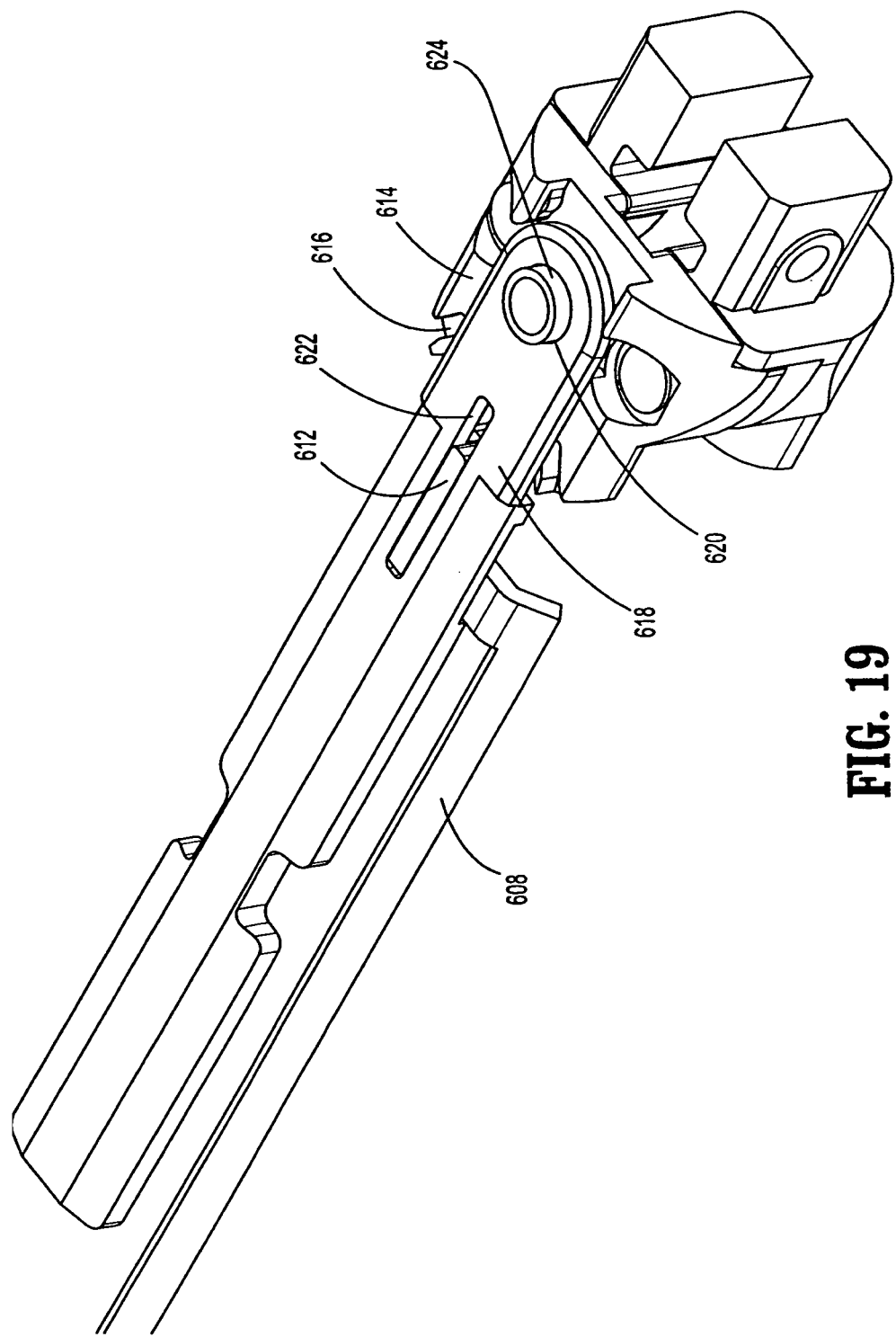
FIG. 19 is an enlarged perspective view of a portion of the locking assembly of FIGS. 16-18 and including a link.
Figure 20:
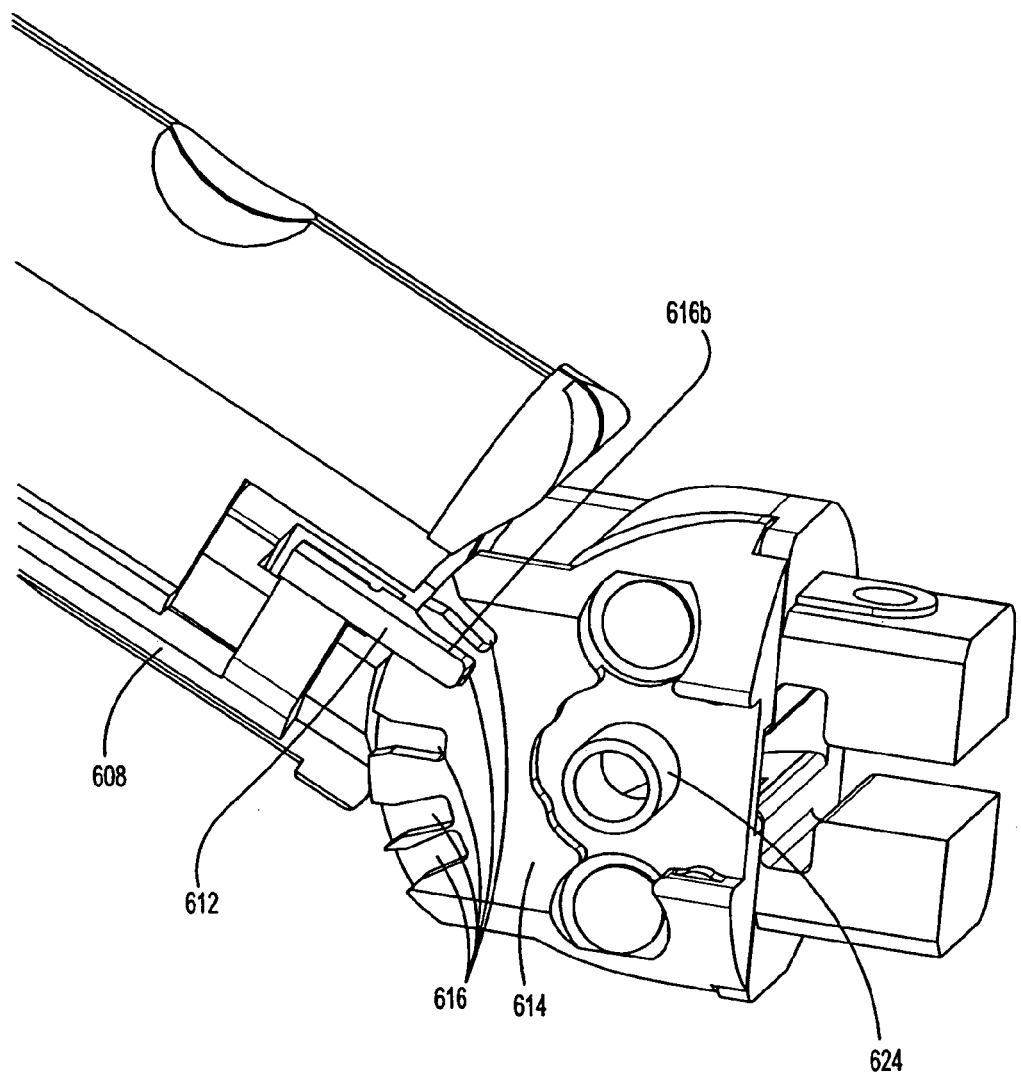
FIG. 20 is an enlarged perspective view of a portion of the locking assembly of FIGS. 16-19 illustrated with the articulating tool assembly in an articulated position.

Now referring to FIGS. 18-20, cam finger 612 and pivot plate 614 are illustrated. Cam finger 612 extends distally from slide 608 and pivot plate 614 may be disposed on mounting assembly 235 (see FIG. 3), for example. It is envisioned that pivot plate 614 may be disposed on or incorporated with a portion of tool assembly 17. A plurality of slots 616 (five slots 616 are illustrated) is disposed on pivot plate 614 and are sized to accept at least a portion of cam finger 612 therein. Upon different amounts of articulation of tool assembly 17 (including no substantial articulation) with respect to body portion 512 (see FIG. 1, for example), cam finger 612 is approximately aligned with an individual slot 616 of pivot plate 614. FIGS. 18 and 19 illustrate cam finger 612 substantially aligned with a center slot 616a (hidden from view in FIG. 19) and FIG. 20 illustrates cam finger 612 substantially aligned with a side slot 616b.

Link 618, illustrated in FIGS. 17 and 19, is in mechanical engagement with pivot plate 614 and cam finger 612. (In FIG. 18, the link has been removed.) Link 618 is illustrated having an opening 620 and a slot 622 (FIG. 19). Opening 620 is in a pivotal relationship with a boss 624 on pivot plate 614 and slot 622 is slidably engaged with cam finger 612. This relationship allows for articulation of pivot plate 614 with respect to body portion 512 and for longitudinal translation of slide 608 with respect to pivot plate 614.

In operation, upon at least a partial actuation of movable handle 516 (see FIG. 1, for example), pusher 604 is forced distally, e.g., via control rod 520 (see FIG. 11, for example), thus causing distal translation of cam finger 612 at least partially into a slot 616 of pivot plate 614. It is envisioned that actuating movable handle 516 to approximate cartridge assembly 18 and an anvil assembly 20 (see FIG. 1A, for example) also functions to translate cam finger 612 distally. In such an embodiment, when articulating tool assembly 17 is in place and clamped on tissue, further articulation cannot be accomplished (without releasing movable handle 516, for example). Thus, locking assembly 600 helps maintain articulating tool assembly 17 in position with respect to body portion 512, prior to emplacing staples into tissue, for example.

As discussed above, spring 610 distally biases slide 608 from rod 606. This biasing provided by spring 610 helps ensure cam finger 612 is not accidentally or prematurely dislodged from slot 616 of pivot plate 614, which may result in a significant amount of "play" therebetween. Additionally, the distal bias provided by spring 610 helps eliminate manufacturing tolerances and/or clearances that are present between slide 608 and pivot plate 614. It is also envisioned that at least a portion of cam finger 612 and/or slot 616 may be wedge-shaped to help reduce any unintended movement therebetween. In such an embodiment, a distal portion of cam finger 612 and slot 616 would be narrower than a corresponding proximal portion.

Figure 21:
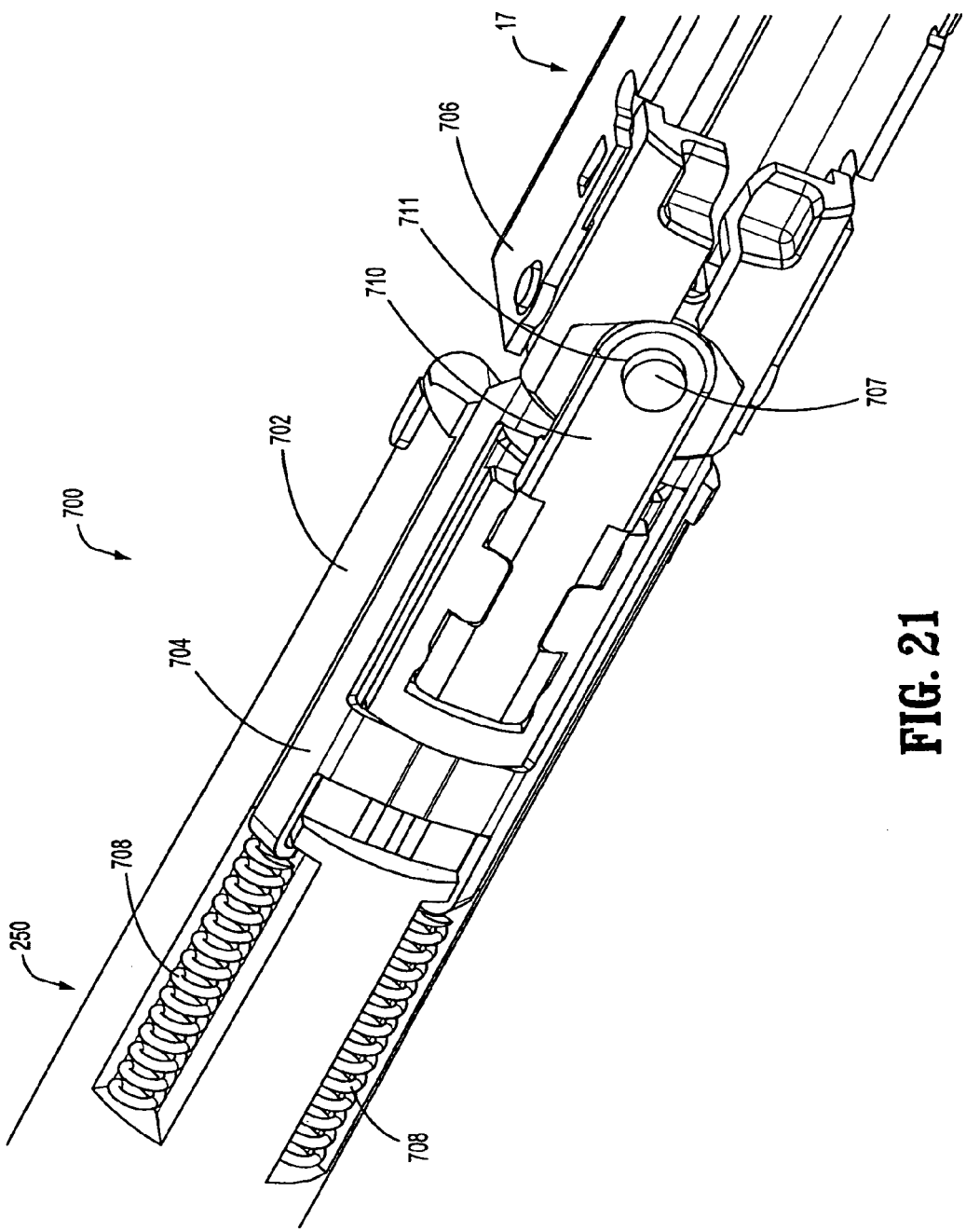
FIG. 21 is an enlarged perspective view of another locking assembly for use with a surgical instrument in accordance with an embodiment of the present disclosure.
Figure 22:
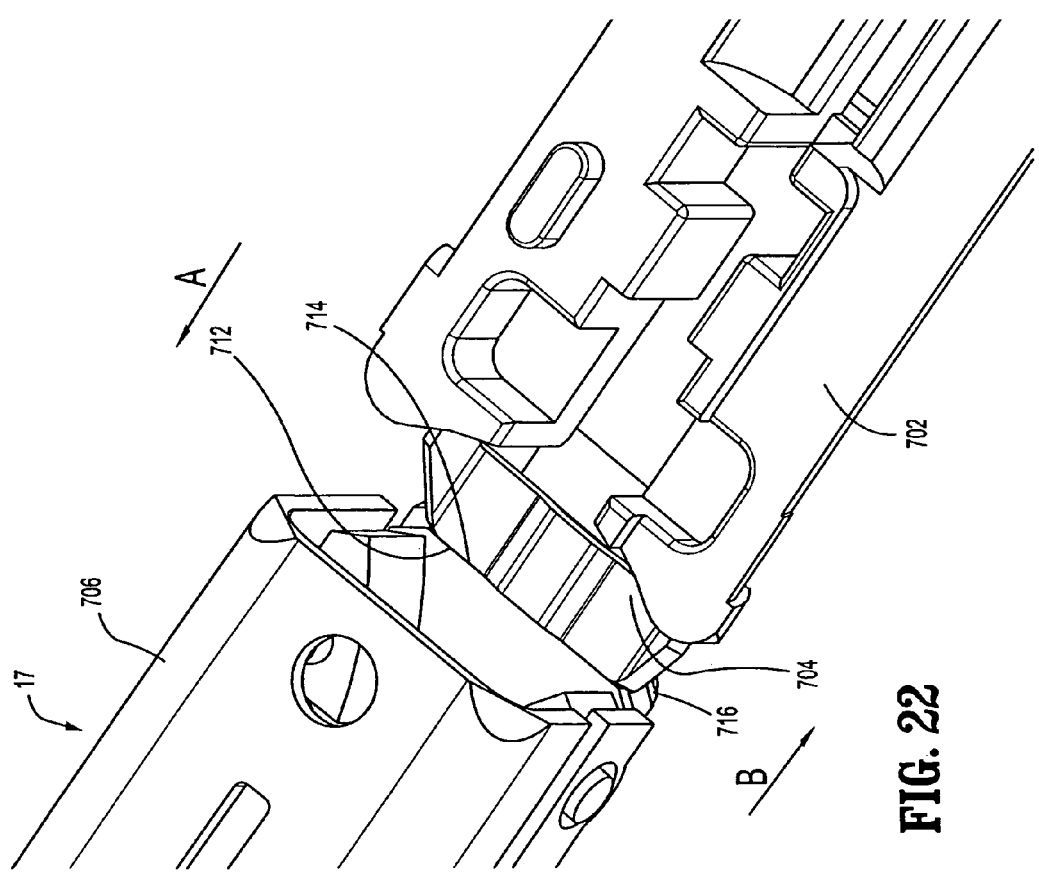
FIG. 22 is an enlarged bottom perspective view of the locking assembly of FIG. 21.

In an embodiment of the present disclosure illustrated in FIGS. 21 and 22, a locking assembly 700 is illustrated for use with surgical instrument 500 and disposable loading unit 16 (see FIG. 1, for example). In the illustrated embodiment, locking assembly 700 includes an adapter 702, a pusher 704, a pivot 706, a biasing element (e.g., a pair of springs 708) and a link 710. Locking assembly 700 generally helps maintain tool assembly 17 in a predetermined position.

With reference to FIG. 21, adapter 702 of locking assembly 700 is generally housed within body portion 512 (see FIG. 1, for example) of surgical instrument 500 or within disposable loading unit 16. In the illustrated embodiment, pusher 704 is located distally of a pair of springs 708. Pusher 704 is distally biased via the pair of springs 708 towards pivot 706 of articulating tool assembly 17. A distal portion of pusher 704 includes a pusher mating surface 712 (FIG. 22) which is shaped and dimensioned to mate with a pivot mating surface 714 (FIG. 22) disposed adjacent a proximal portion of pivot 706. Link 710 is illustrated in mechanical cooperation with a portion of pusher 704 and pivotably connected to a portion of pivot 706, thus allowing articulating tool assembly 17 to move between its first position and its second position with respect to body portion 512. More specifically, link 710 includes an opening 711 that fits over a protrusion 707 of pivot 706, thus allowing pivotal movement therebetween. Further, link 710 is slidably engaged with a portion of adapter 702, thus allowing longitudinal movement therebetween.

Now referring to FIG. 22, pusher mating surface 712 is substantially flat along a majority of its length in this embodiment. Correspondingly, pivot mating surface 714 is also flat along a majority of its length in the illustrated embodiment. Thus, the distal bias of pusher 704 towards pivot 706 (in the direction of arrow A) via the pair of springs 708, helps maintain articulating tool assembly 17 in its first, non-articulated, position, as the biasing force helps articulating tool assembly 17 resist pivoting. While two springs 708 are illustrated, more or fewer springs 708 may be provided.

To pivot articulating tool 17 from its first, non-articulated position, the distal biasing force from pair of springs 708 must be overcome. Such a pivoting action, moves pusher 704 proximally (in the direction of arrow B) against the bias of pair of springs 708. It is also envisioned that pusher mating surface 714 includes detents (not explicitly shown in this embodiment) to help stabilize articulating jaw member 17 in selected articulated positions.

With continued reference to FIG. 22, pivot 706 includes a shelf 716 thereon. As shown in FIG. 22, shelf 716 overlaps at least a portion of pusher 704 when pusher mating surface 712 is in contact with pivot mating surface 714. Shelf 716 is situated and configured to help prevent tissue from being pinched between pusher 704 and pivot 706 when articulating tool assembly 17 is rotated and/or articulated.

Figure 23:
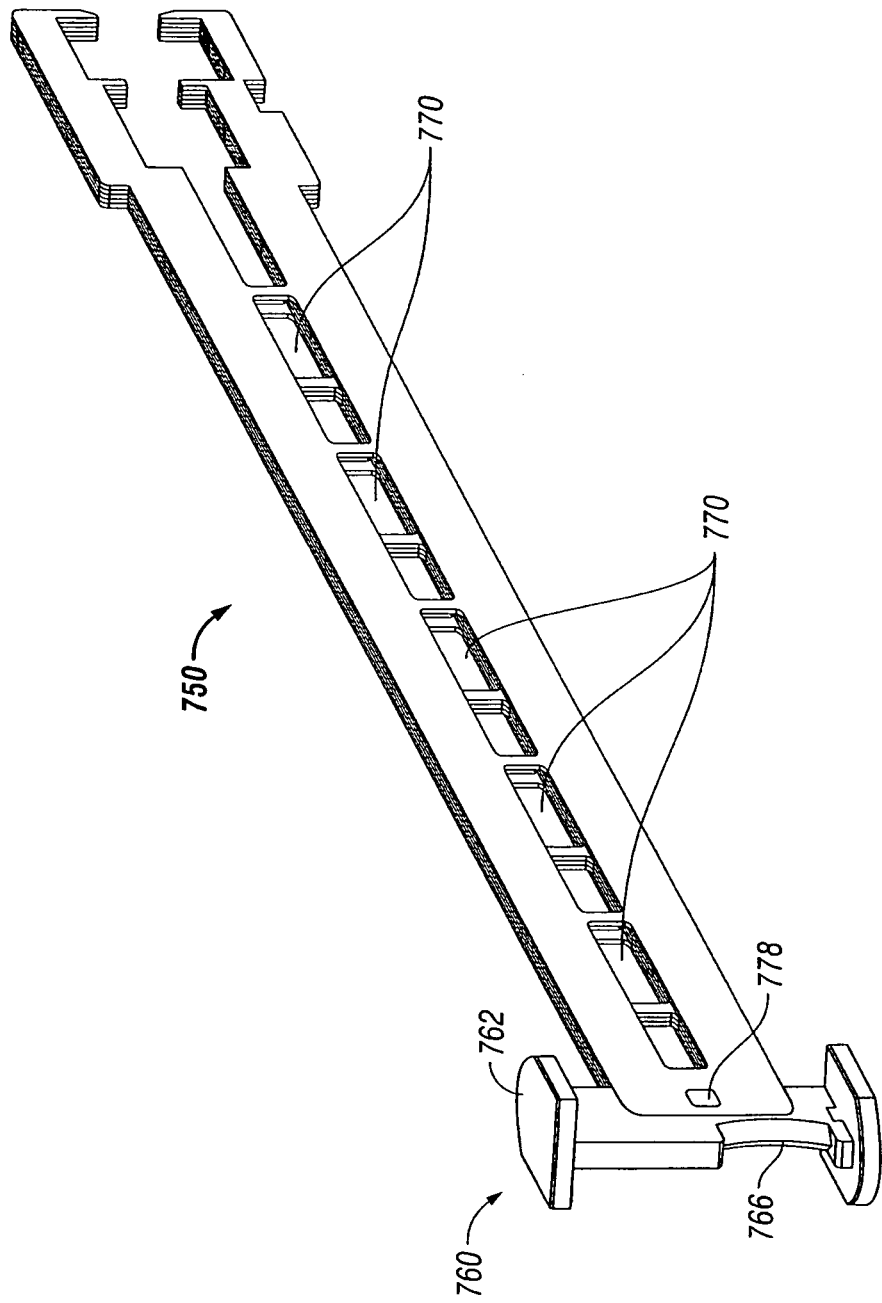
FIG. 23 is a perspective view of a drive beam having a plurality of layers and a closure apparatus in accordance with an embodiment of the present disclosure.
Figure 24:
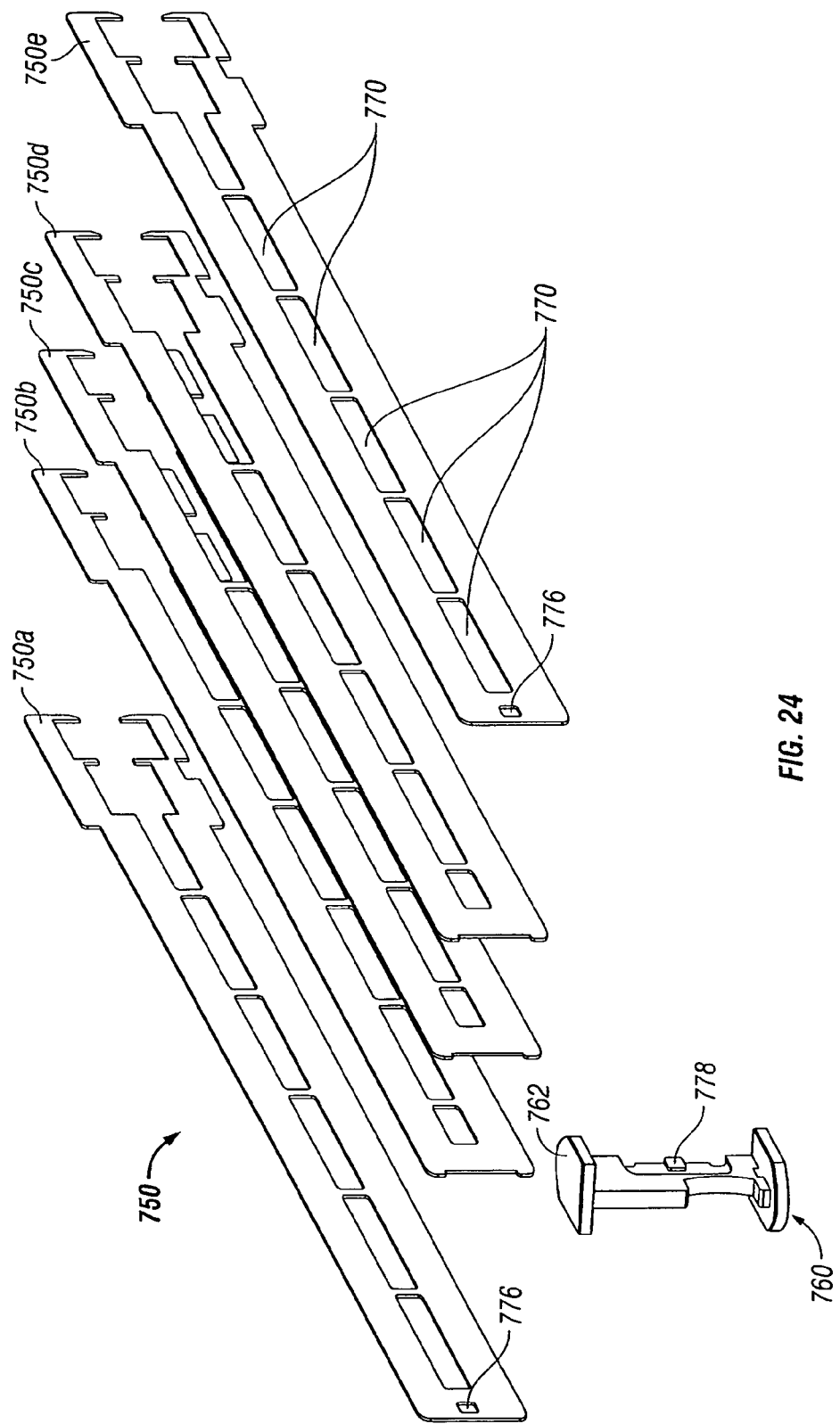
FIG. 24 is a perspective view of the drive beam and closure apparatus of FIG. 23 with parts separated.
Figure 25:
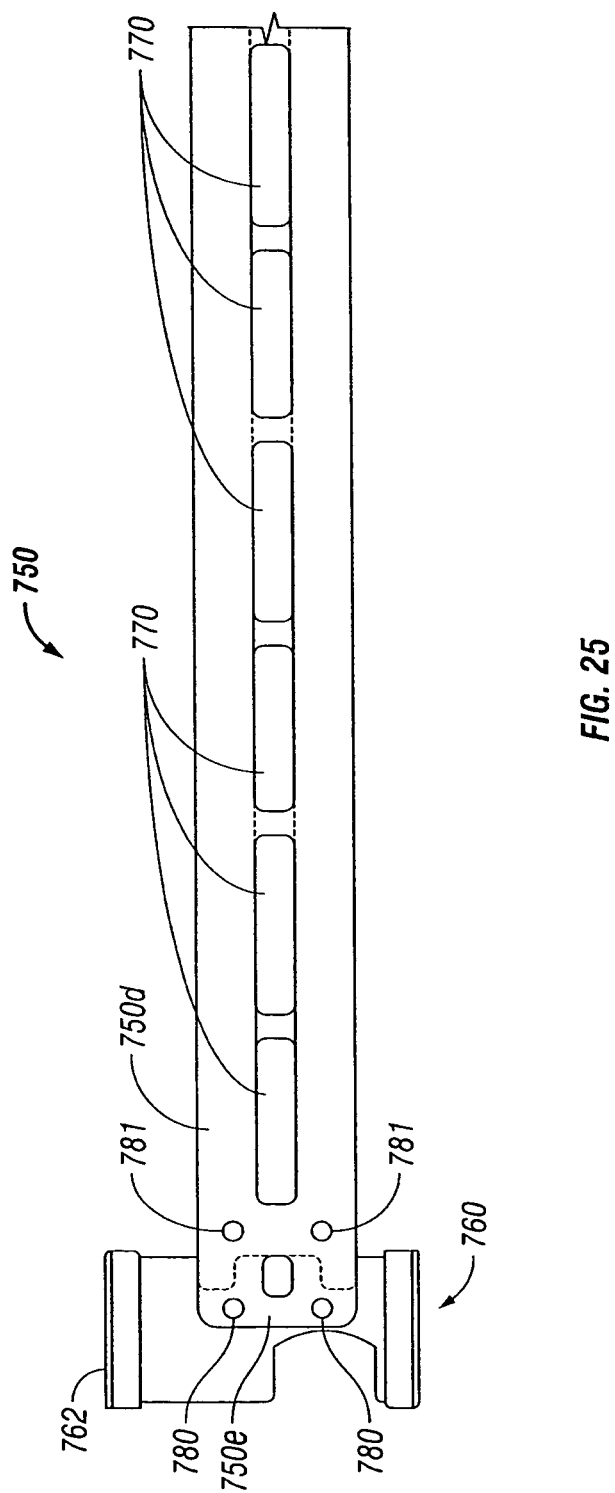
FIG. 25 is a cross-sectional view of a portion of the drive beam and closure apparatus of FIGS. 23 and 24.

In an embodiment of the present disclosure illustrated in FIGS. 23-25, a multi-layered drive beam 750 having a plurality of layers 750a-750e is illustrated and may be included in a disposable loading unit 16 (see FIG. 1, for example). A closure apparatus 760, such as an I-beam, is also illustrated. Closure apparatus 760 includes a horizontal portion 762 that is advanceable into camming surface 42 (or other contact surface) to approximate tool assembly tool assembly 17, as described in detail above with reference to FIG. 2.

With reference to FIG. 24, multi-layered drive beam 750 having five layers 750a-750e is illustrated. It is envisioned and within the scope of the present disclosure that fewer or more layers may be used to form multi-layered drive beam 750. It is also envisioned that multi-layered drive beam 750 may replace drive beam 266 in other embodiments of this disclosure. Use of multi-layered drive beam 750 may provide increased strength and flexibility during use, specifically, for instance, while tool assembly 17 is in an articulated position.

A plurality of cutouts 770 is illustrated in FIGS. 23-25 which extend through each layer of multi-layered drive beam 750. Although the figures show between five and ten cutouts per layer of multi-layered drive beam 750, the exact number of cutouts 770 may be fewer than five, between five and ten, or greater than ten. Additionally, cutouts 770 of adjacent layers of drive beam 750 may or not align with each other. The use of cutouts 770 reduces cross-sectional dimensions of drive beam 750 and allows for bending force adjustment. While rectangular cutouts 770 are illustrated, the use of cutouts 770 having other regular or non-regular shapes is also contemplated.

The attachment of each layer 750a-750e of multi-layered drive beam 750 and the attachment to closure apparatus 760 are illustrated in FIG. 25. In the illustrated embodiment, an outer layer (750a or 750e of FIG. 24) is affixed to closure apparatus 760 in two locations (each location being indicated by numeral 780 in FIG. 25), via a pair of spot welds, for example. It is also envisioned that each outer layer 750a, 750e includes an aperture 776 that fits over a boss 778 protruding from closure apparatus 760. Each outer layer 750a, 750e is also affixed to an adjacent layer (e.g., 750b or 750d) in two locations (each location being indicated by numeral 781 in FIG. 25), possibly via a pair of spot welds. Further, each inner layer (e.g., 750b, 750c and 750d) is attached to an adjacent inner layer (for instance, 750b is attached to 750c; 750c is attached to 750b and 750d; and 750d is attached to 750c) in two locations, via spot welds, for example. While spot welding is disclosed as an attachment method, other methods for attaching each layer to each other and the outer layers to the closure apparatus are envisioned and within the scope of the present disclosure. The illustrated embodiments show attachments points 780 of inner layers adjacent closure apparatus 760, but it is envisioned and within the scope of the present disclosure that attachment points 780 are disposed in other locations on drive beam 750. Additionally, it is envisioned that at least one layer of drive beam 750 is made of a metal, such as stainless steel. Portions of drive beam 750 and/or closure apparatus 760 may also be made of or at least partially coated with a plastic material, as described below. Further, closure apparatus 790 may include a cutting surface 766 (FIG. 23) thereon for cutting tissue.

Figure 26:
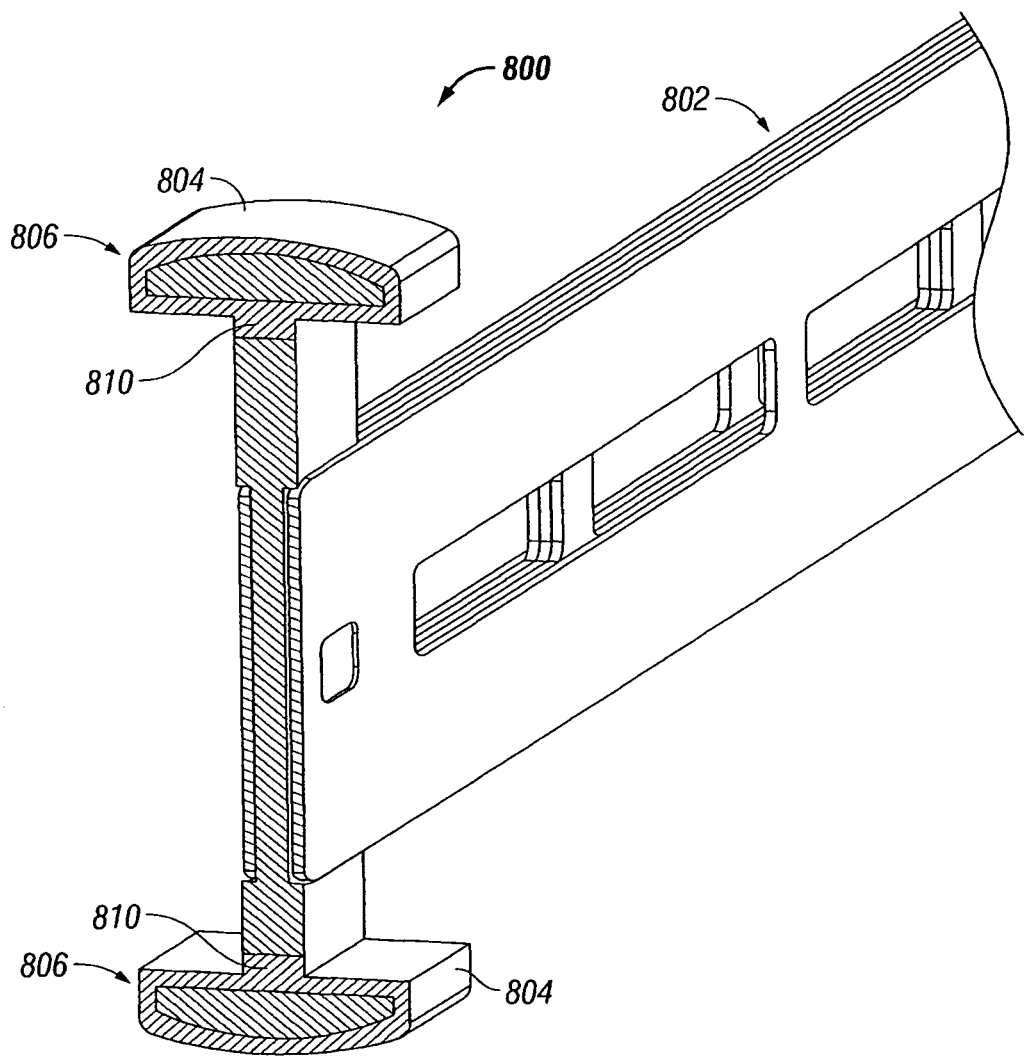
FIG. 26 is a cross-sectional view of a drive beam and a closure apparatus in accordance with an embodiment of the present disclosure.
Figure 27:
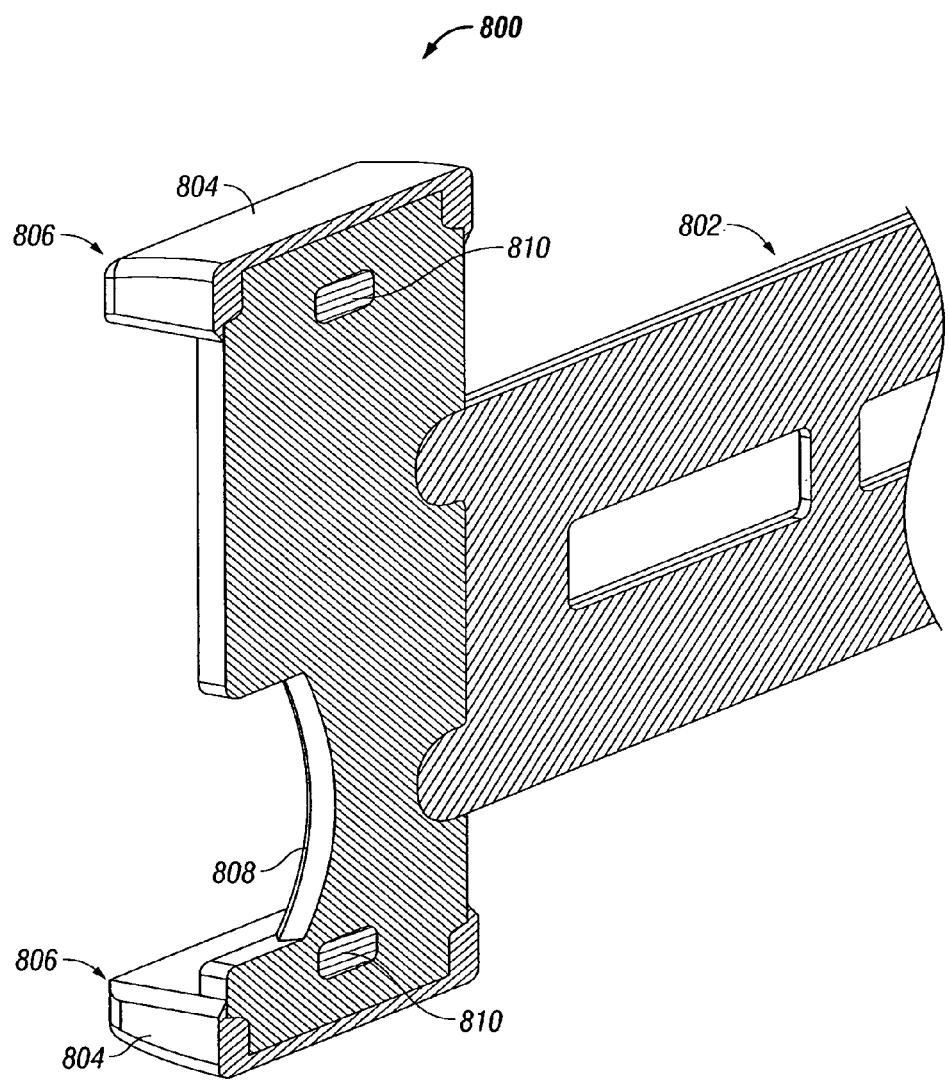
FIG. 27 is a cross-sectional view of the drive beam and closure apparatus of FIG. 26.

In an embodiment of the present disclosure illustrated in FIGS. 26 and 27, a closure apparatus 800 and a portion of drive beam 802 are shown. Closure apparatus and/or a contact surface (e.g., camming surface 42) of tool assembly 17 (see FIG. 2, for example) may include a plastic surface or plastic coating. In this embodiment, closure apparatus 800 is illustrated having a pair of caps 804 at least partially covering horizontal portions 806 of closure apparatus 800. Caps 804 may be made of plastic in this embodiment. Such plastic surfaces disposed on closure apparatus 800 and/or contact surface of tool assembly 17 generally reduce the amount of friction therebetween vis-à-vis two metal surfaces. That is, a plastic to metal or a plastic to plastic interaction may create less friction than interaction between a pair of metal surfaces. This reduced amount of friction may correspond to a reduced firing force.

It is envisioned that a portion of closure apparatus 800, such as pair of caps 804, is made of plastic, overmolded with plastic or includes a plastic coating. Additionally, a contact surface of tool assembly 17, or at least a portion thereof, may also be made of plastic, be overmolded with plastic or include a plastic coating.

In an embodiment of the disclosure, closure apparatus 800 may include an I-shaped cross section, as illustrated in FIGS. 26 and 27. Additionally, closure apparatus 800 and drive beam 802 may be part of a disposable loading unit 16 and/or part of a surgical instrument 500 that is able to articulate. Further, drive beam 802 may include a single layer or a plurality of layers (as shown in FIG. 26) and at least a portion of drive beam 802 may be made of plastic. Still further, closure apparatus 800 may include a cutting surface 808 (FIG. 27) thereon for cutting tissue.

With continued reference to FIGS. 26 and 27, plastic cap 804 may include a reinforced section 810 which may increase the strength of closure apparatus 800 or may provide a stronger connection between cap 804 and horizontal portion 806 of closure apparatus 800. It is also envisioned that cap 804 may be removably attached to closure apparatus 800. In such an embodiment, cap 804 may be removed and replaced if any substantial wearing or damage occurs.

Figure 28:
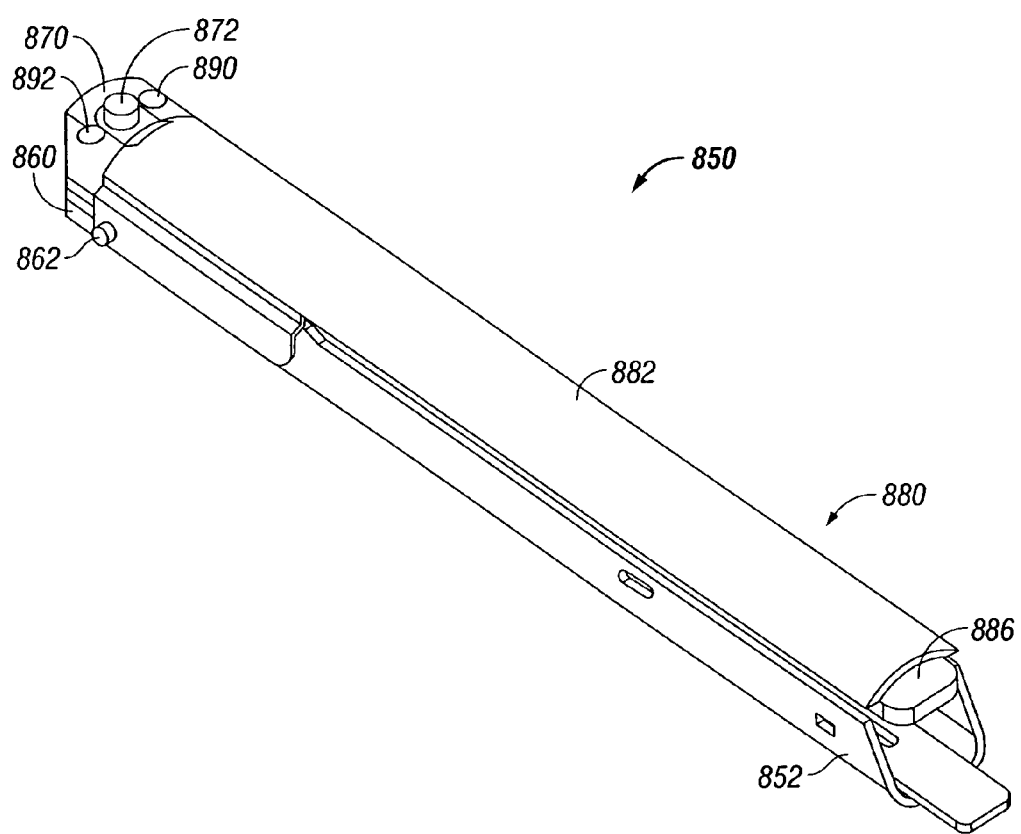
FIG. 28 is a perspective view of a tool assembly in accordance with an embodiment of the present disclosure.
Figure 29:
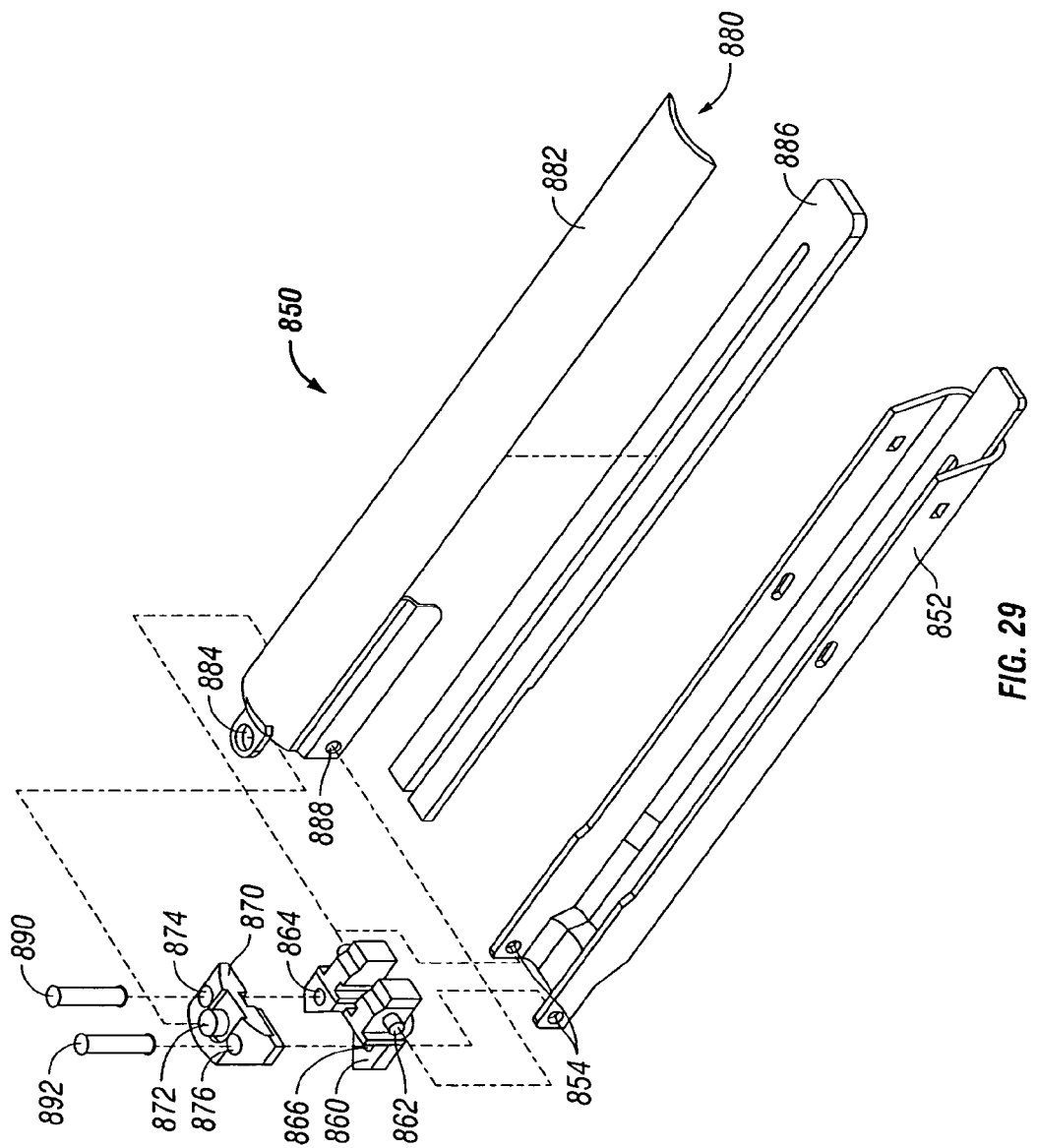
FIG. 29 is an assembly view of the tool assembly of FIG. 28.

In an embodiment of the present disclosure illustrated in FIGS. 28 and 29, a tool assembly 850 is illustrated. Tool assembly 850 of this embodiment includes a channel 852, a first attachment member 860, a second attachment member 870, an anvil assembly 880, a first attachment rod 890 and a second attachment rod 892. First and second attachment rods 890, 892 provide a strong connection facilitating the elements of tool assembly 850 to remain together.

Channel 852 includes an opening 854 (two openings are illustrated) adjacent its proximal end and first attachment member 860 includes a boss 862 (two bosses are illustrated) extending therefrom. Channel 852 is connectable to first attachment member by placing opening(s) 854 over boss(es) 862, thus providing a pivotal connection therebetween. Although not explicitly illustrated in the present embodiment, channel 852 may house a plurality of surgical fasteners or a staple cartridge.

Anvil assembly 880 includes an anvil cover 882 and an anvil 886. Anvil 886 is configured for mechanical engagement with anvil cover 882, e.g., via a snap-fit connection. An aperture 884 extends at least partially through a portion of anvil cover 882. Aperture 884 is configured to fit over a protrusion 872 disposed on second attachment member 870, thereby providing a connection between anvil assembly 880 and second attachment member 870. Additionally, anvil cover 882 includes at least one opening 888 extending at least partially therethrough in an embodiment of the disclosure. Opening 888 is configured to fit over boss 862 of first attachment member 860. In such an embodiment, anvil assembly 880 may be pivoted with respect to first attachment member 860 and second attachment member 870.

First attachment member 860 includes a first opening 864 and a second opening 866 extending therethrough. Second attachment member 870 also includes a first opening 874 and a second opening 876 extending therethrough (FIG. 29). Further, first attachment member 860 and second attachment member 870 are in mechanical engagement, such that first openings 864, 874 substantially align and second openings 866, 876 substantially align.

To secure first attachment member 860 with second attachment member 870 (and thus channel 852 and anvil assembly 880), first attachment rod 890, or a portion thereof, is inserted through first openings 864 and 874. To further secure the elements of tool assembly 850, second attachment rod 892, or a portion thereof, is inserted through second openings 866 and 876. It is envisioned that first attachment rod 890 and/or second attachment rod 892 are rivets, such as two-part rivets that are tightenable.

In an embodiment of the disclosure, tool assembly 850 is part of a disposable loading unit, which may be able to articulate. Articulation of tool assembly 850 may be facilitated by pivotably attaching tool assembly 850 to a body portion of a surgical instrument via protrusion 874 extending from second attachment member 870 and a link (such as link 710 in FIG. 21). Additionally, a method of assembling tool assembly 850, as described above, is contemplated by the present disclosure.

It will be understood that various modifications may be made to the embodiments disclosed herein. For example, the above-described lock assembly may be incorporated into a variety of surgical instruments which include DLUs and is not limited to use on linear staplers. Further, the DLU may be configured to receive an insertion tip of surgical instrument in contrast to that disclosed. Therefore, the above description should not be construed as limiting, but merely as exemplifications of various embodiments. Those skilled in the art will envision other modifications within the scope and spirit of the claims appended hereto.

What is claimed is:

1. A surgical instrument, comprising:
   a handle portion;
   a body portion extending distally from the handle portion and defining a first longitudinal axis;
   a movable handle disposed on the handle portion and in mechanical cooperation with a drive member;
   a tool assembly including an anvil, a cartridge assembly and a contact surface, the tool assembly being supported adjacent a distal end of the body portion;
   a drive beam including a plurality of layers, at least one layer having a proximal engagement portion disposed adjacent a proximal end thereof and being configured to engage a portion of the drive member;
   a closure apparatus disposed adjacent a distal end of the drive beam being configured to engage the contact surface of the tool assembly, whereby at least a partial actuation of the movable handle moves the closure apparatus distally into engagement with the contact surface to approximate the anvil and the cartridge assembly; and
   wherein at least one of the plurality of layers of the drive beam is affixed to an adjacent layer of the drive beam via at least one spot weld, and wherein the drive beam includes two outer layers and at least two inner layers, the two outer layers being affixed to the closure apparatus in at least one location.

2. The surgical instrument of claim 1, wherein the drive beam includes between four layers and six layers.

3. The surgical instrument of claim 1, wherein the drive beam includes five layers.

4. The surgical instrument of claim 1, wherein at least one layer of the drive beam is made of stainless steel.

5. The surgical instrument of claim 1, wherein each layer of the drive beam is made of stainless steel.

6. The surgical instrument of claim 1, wherein all of the plurality of layers of the drive beam are affixed to each other.

7. The surgical instrument of claim 1, wherein all of the plurality of layers of the drive beam are spot welded to each other in at least one location.

8. The surgical instrument of claim 1, wherein the closure apparatus includes a cutting surface thereon.

9. The surgical instrument of claim 1, wherein the two outer layers of the drive beam are affixed to at least one inner layer in at least one location, and the at least two inner layers being affixed to an adjacent inner layer in at least one location.

10. The surgical instrument of claim 9, wherein all of the plurality of layers of the drive beam are affixed to adjacent layers of the drive beam via at least one spot weld.

11. The surgical instrument of claim 1, wherein a cross-section of the closure apparatus is generally I-shaped.

12. The surgical instrument of claim 1, wherein each of the plurality of layers of the drive beam include a plurality of cutouts disposed therethrough.

13. The surgical instrument of claim 1, wherein the drive beam is part of a disposable loading unit.

14. The surgical instrument of claim 1, wherein the two outer layers of the drive beam extend farther distally than the two inner layers of the drive beam.

15. A disposable loading unit, comprising:
  a drive beam including a plurality of layers and defining a first longitudinal axis;
  an articulating tool assembly disposed distally of the drive beam and defining a second longitudinal axis, the articulating tool assembly including an anvil, a cartridge assembly and a contact surface and being movable from a first position in which the second longitudinal axis is substantially aligned with the first longitudinal axis to a second position in which the second longitudinal axis is disposed at an angle to the first longitudinal axis;
  a closure apparatus disposed adjacent a distal end of the drive beam being configured to engage the contact surface of the articulating tool assembly, whereby distal movement of the drive beam moves the closure apparatus distally into engagement with the contact surface to approximate the anvil and the cartridge assembly; and
  wherein at least one of the plurality of layers of the drive beam is affixed to an adjacent layer of the drive beam via at least one spot weld, and wherein the drive beam includes two outer layers and at least two inner layers, the two outer layers being affixed to the closure apparatus in at least one location.

16. The disposable loading unit of claim 15, wherein the drive beam includes between four layers and six layers.

17. The disposable loading unit of claim 15, wherein at least one layer of the drive beam is made of stainless steel.

18. The disposable loading unit of claim 15, wherein all of the plurality of layers of the drive beam are spot welded to each other in at least one location.

19. The disposable loading unit of claim 15, wherein the two outer layers of the drive beam are affixed to at least one inner layer in at least one location, and the at least two inner layers being affixed to an adjacent inner layer in at least one location.

20. The disposable loading unit of claim 19, wherein all of the plurality of layers of the drive beam are affixed to adjacent layers of the drive beam via at least one spot weld.

21. The disposable loading unit of claim 15, wherein the two outer layers of the drive beam extend farther distally than the two inner layers of the drive beam.

* * * * *